US011083705B2

(12) United States Patent
Semba et al.

(10) Patent No.: US 11,083,705 B2
(45) Date of Patent: Aug. 10, 2021

(54) PHARMACEUTICAL COMPOSITION FOR TREATING TUMOR

(71) Applicant: Eisai R&D Management Co., Ltd., Tokyo (JP)

(72) Inventors: Taro Semba, Tsukuba (JP); Yasuhiro Funahashi, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/835,719

(22) Filed: Mar. 31, 2020

(65) Prior Publication Data

US 2021/0023047 A1    Jan. 28, 2021

(30) Foreign Application Priority Data

Jul. 26, 2019    (JP) ............................ JP2019-138041

(51) Int. Cl.
| A61K 31/357 | (2006.01) |
| A61K 9/127 | (2006.01) |
| A61P 35/00 | (2006.01) |
| C07K 16/28 | (2006.01) |
| A61P 35/04 | (2006.01) |

(52) U.S. Cl.
CPC ............ *A61K 31/357* (2013.01); *A61P 35/04* (2018.01); *C07K 16/2818* (2013.01); *A61K 9/127* (2013.01)

(58) Field of Classification Search
CPC ........ A61K 31/357; A61K 9/127; A61P 35/00
See application file for complete search history.

(56) References Cited

U.S. PATENT DOCUMENTS

| 5,192,549 | A | 3/1993 | Barenolz et al. |
| 5,316,771 | A | 5/1994 | Barenolz et al. |
| 5,571,534 | A | 11/1996 | Jalonen et al. |
| 5,736,155 | A | 4/1998 | Bally et al. |
| 5,759,573 | A | 6/1998 | Kim |
| 5,821,349 | A | 10/1998 | Djedaini-Pilard et al. |
| 6,051,251 | A | 4/2000 | Zalipsky et al. |
| 6,214,865 | B1 | 4/2001 | Littlefield et al. |
| 6,469,182 | B1 | 10/2002 | Littlefield et al. |
| 6,653,341 | B1 | 11/2003 | Littlefield et al. |
| 6,747,011 | B1 | 6/2004 | Zhang |
| 7,488,802 | B2 | 2/2009 | Collins et al. |
| 7,521,051 | B2 | 4/2009 | Collins et al. |
| 7,982,060 | B2 | 7/2011 | Austad et al. |
| 8,008,449 | B2 | 8/2011 | Korman et al. |
| 8,093,410 | B2 | 1/2012 | Chase et al. |
| 8,168,757 | B2 | 5/2012 | Finnefrock et al. |
| 8,350,067 | B2 | 1/2013 | Endo et al. |
| 8,354,509 | B2 | 1/2013 | Carven et al. |
| 8,383,796 | B2 | 2/2013 | Korman et al. |
| 9,968,583 | B2 | 5/2018 | Kikuchi et al. |
| 2002/0131995 | A1 | 9/2002 | Szoka |
| 2004/0156889 | A1 | 8/2004 | Hu et al. |
| 2005/0118249 | A1 | 6/2005 | Webb et al. |
| 2005/0118250 | A1 | 6/2005 | Tardi et al. |
| 2006/0008909 | A1 | 1/2006 | Cullis et al. |
| 2006/0104984 | A1 | 5/2006 | Littlefield et al. |
| 2006/0147511 | A1 | 7/2006 | Panzer et al. |
| 2007/0112176 | A1 | 5/2007 | Seiki et al. |
| 2007/0116753 | A1 | 5/2007 | Hong et al. |
| 2007/0155696 | A1 | 7/2007 | Ishihara et al. |
| 2007/0244187 | A1 | 10/2007 | Austad et al. |
| 2009/0196913 | A1 | 8/2009 | Huang et al. |
| 2009/0196918 | A1 | 8/2009 | Joguparthi et al. |
| 2010/0247629 | A1 | 9/2010 | Gabizon et al. |
| 2011/0018419 | A1 | 1/2011 | Suzuki et al. |
| 2011/0184190 | A1 | 7/2011 | Endo et al. |
| 2011/0262524 | A1 | 10/2011 | Bally et al. |
| 2011/0271358 | A1 | 11/2011 | Freeman et al. |
| 2012/0058178 | A1* | 3/2012 | Kikuchi ............... A61K 9/1271 424/450 |
| 2012/0128757 | A1 | 5/2012 | Kikuchi et al. |
| 2014/0044777 | A1 | 2/2014 | Kikuchi et al. |
| 2014/0212479 | A1 | 7/2014 | Zeinelden |
| 2014/0248263 | A1 | 9/2014 | Andersen et al. |
| 2015/0005343 | A1 | 1/2015 | Nomoto et al. |
| 2015/0246033 | A1 | 9/2015 | Flynn et al. |
| 2016/0338954 | A1 | 11/2016 | Brinker et al. |
| 2017/0020817 | A1 | 1/2017 | Singh |
| 2017/0071903 | A1 | 3/2017 | Funahashi et al. |
| 2018/0071247 | A1 | 3/2018 | Matsui et al. |
| 2019/0111022 | A1 | 4/2019 | Asano et al. |
| 2019/0263927 | A1 | 8/2019 | Olivo |

FOREIGN PATENT DOCUMENTS

| CA | 2673924 | 7/2008 |
| CN | 101209243 | 7/2008 |
| CN | 103562406 | 2/2014 |
| CN | 105640935 | 6/2016 |
| EP | 1332755 | 8/2003 |

(Continued)

OTHER PUBLICATIONS

Golub et al., Science, vol. 286, Oct. 15, 1999, pp. 531-537.*
[No Author], "Ammonium Cations," The Illustrated Glossary of Organic Chemistry, [Retrieved on Mar. 9, 2016], retrieved from: URL<http://www.chem.ucla.edu/harding/IGOC/A/ammonium_cation.html>, 1 page.
[No Author], "Halaven Intravenour Injection 1mg," Package Insert for Halaven, Eisai, Ltd., Jul. 2011, 6 pages (with partial English Translation).
[No Author], "Novantron Infection 10mg, 20mg," Package Insert, ASKA Pharmaceutical Co., Ltd., Nov. 2011, 6 pages (with partial English Translation).

(Continued)

*Primary Examiner* — Samira J Jean-Louis
(74) *Attorney, Agent, or Firm* — Fish & Richardson P.C.

(57) ABSTRACT

Disclosed herein is a method for treating tumor, comprising administering a liposomal composition comprising eribulin or a pharmaceutically acceptable salt thereof and a PD-1 antagonist to a patient in need thereof.

17 Claims, 4 Drawing Sheets

(56) References Cited

FOREIGN PATENT DOCUMENTS

| | | |
|---|---|---|
| EP | 1921086 | 5/2008 |
| EP | 2123260 | 11/2009 |
| EP | 2415464 | 2/2012 |
| JP | H07-501813 | 2/1995 |
| JP | H08-509230 | 10/1996 |
| JP | 2002-518384 | 6/2002 |
| JP | 2004-516247 | 6/2004 |
| JP | 2005-509000 | 4/2005 |
| JP | 2006-513189 | 4/2006 |
| JP | 2006-340714 | 12/2006 |
| JP | 2010-514708 | 5/2010 |
| JP | 5551683 | 5/2014 |
| JP | 2018-508516 | 3/2018 |
| WO | WO 1993/011757 | 6/1993 |
| WO | WO 1994/023697 | 10/1994 |
| WO | WO 1999/065894 | 12/1999 |
| WO | WO 2002/032399 | 4/2002 |
| WO | WO 2003/041681 | 5/2003 |
| WO | WO 2004/004771 | 1/2004 |
| WO | WO 2004/056875 | 7/2004 |
| WO | WO 2004/058140 | 7/2004 |
| WO | WO 2004/072286 | 8/2004 |
| WO | WO 2005/046643 | 5/2005 |
| WO | WO 2005/118565 | 12/2005 |
| WO | WO 2006/037230 | 4/2006 |
| WO | WO 2007/026869 | 3/2007 |
| WO | WO 2007/061874 | 5/2007 |
| WO | WO 2008/080367 | 7/2008 |
| WO | WO 2008/156712 | 12/2008 |
| WO | WO 2010/027827 | 3/2010 |
| WO | WO 2010/077634 | 7/2010 |
| WO | WO 2010/113983 | 10/2010 |
| WO | WO 2010/113984 | 10/2010 |
| WO | WO 2011/066342 | 6/2011 |
| WO | WO 2011/094339 | 8/2011 |
| WO | WO 2012/135408 | 10/2012 |
| WO | WO 2013/019906 | 2/2013 |
| WO | WO 2014/087230 | 6/2014 |
| WO | WO 2014/159562 | 10/2014 |
| WO | WO 2014/193898 | 12/2014 |
| WO | WO 2014/208774 | 12/2014 |
| WO | WO 2015/112900 | 7/2015 |
| WO | WO 2015/134399 | 9/2015 |
| WO | WO 2015/134605 | 9/2015 |
| WO | WO 2015/184145 | 12/2015 |
| WO | WO-2016141209 A1 * 9/2016 ............ A61P 15/00 |
| WO | WO 2017/188350 | 11/2017 |
| WO | WO 2018/071792 | 4/2018 |

OTHER PUBLICATIONS

[No Author], WHO Drug Information, 2013, vol. 27, No. 1, pp. 68-69.

[No Author], WHO Drug Information, 2013, vol. 27, No. 2, pp. 161-162.

Adams et al., "Phase 2 study of pembrolizumab (pembro) monotherapy for previously treated metastatic triple-negative breast cancer (mTNBC): KEYNOTE-086 cohort A," Journal of Clinical Oncology, 2017, 35(15 suppl):1008.

Adams et al., "Phase 2 study of pembrolizumab as first-line therapy for PD-L1-positive metastatic triple-negative breast cancer (mTNBC): Preliminary data from KEYNOTE-086 cohort B," Journal of Clinical Oncology, 2017, 35(15 suppl):1088.

Ahmadzadeh et al., "Tumor antigen-specific CD8 T cells infiltrating the tumor express high levels of PD-1 and are functionally impaired," Blood, 2009, 114(8):1537-1544.

Applicant Observation filed in Chinese Patent Application No. 201080014698.2, dated Apr. 2, 2013 to the first Chinese Office Action dated Oct. 24, 2012, 48 pages (with English Translation).

Arima et al., "Enhancement of antitumor effect of doxorubicin by its complexation with γ-cyclodextrin in pegylated liposomes," Journal of Drug Targeting, 2006, 14(4):225-232.

Asano et al., "Broad-spectrum Preclinical Antitumor Activity of Eribulin (Halaven®): Combination with Anticancer Agents of Differing Mechanisms," Anticancer Research, 2018, 38:3375-3385.

Beijnen et al., "Aspects of the degradation kinetics of doxorubicin in aqueous solution," International Journal of Pharmaceutics, Elsevier, 1986, 32:123-131.

Bolotin et al., "Ammonium sulfate gradients for efficient and stable remote loading of amphipathic weak bases into liposomes and ligandoliposomes," Journal of Liposome Research, 1994, 4(1):455-479, XP000572717.

Cardoso et al., "ESO-ESMO 2nd international consensus guidelines for advanced breast cancer (ABC2)," The Breast, 2014, 23:489-502.

ClinicalTrials.gov [online], "An open-label Multicenter Multiple Dose Phase 1 Study to Establish the Maximum Tolerated Dose of E7389 Liposomal Formulation in Patients With Solid Tumors," Apr. 2016, National Library of Medicine, Bethesda MD, USA,—NCT01945710, retrieved from: URL<https://clinicaltrials.gov/archive/NCT01945710/2016_04_19>, 6 pages.

ClinicalTrials.gov [online], "Study NCT01848834—Study of MK-3475 in Participants With Advanced Solid Tumors (MK-3475-012/KEYNOTE-012," Apr. 2014, retrieved from: URL<https://clinicaltrials.gov/ct2/history/NCT01848834?V_24=View>, 7 pages.

Coates et al., "Tailoring therapies—improving the management of early breast cancer: St Gallen International Expert Consensus on the Primary Therapy of Early Breast Cancer 2015," Annals of Oncology, 2015, 26(8):1533-1546.

Communication under Rule 71(3) EPC in European Patent Application No. 10758754.5, dated Jan. 19, 2017, 54 pages.

Communication under Rule 71(3) EPC in European Patent Application No. 10758755.2, dated Feb. 25, 2016, 7 pages.

Completion of Final Requirements in Philippine Patent Application No. 1-2011-501838, dated Aug. 27, 2015, 1 page.

Cortes et al., "Eribulin monotherapy versus treatment of physician's choice in patients with metastatic breast cancer (EMBRACE): a phase 3 open-label randomised study," Lancet, 2011, 377:914-923.

CTEP Rapid Communication, "Solicitation for Letters of Intent: Clinical trials—Preclinical experiments, E7389, Halichondrin B analog (NSC 707389)," 11 pages.

Cullis et al., "pH Gradients and Membrane Transport in liposomal Systems," Trends in Biotechnology, 1991. 9(8)268-272.

Danhier et al., "Strategies to improve the EPR effect for the delivery of anti-cancer nanomedicines," Cancer Cell & Microenvironment, 2015, 2:e808.

Decision on Grant in Russian Application No. 2011139715, dated Sep. 25, 2012, 14 pages (with English Translation).

Decision to Grant in Japanese Patent Application No. 2011-507239, dated Aug. 27, 2014, 5 pages (with English Translation).

Decision to Grant in Japanese Patent Application No. 2011-507240, dated May 7, 2014, 5 pages (with English Translation).

Decision to Grant in Japanese Patent Application No. 2014-092382, dated Jun. 2, 2015, 6 pages (with English Translation).

DesJardins et al., "A high-performance liquid chromatography-tandem mass spectrometry method for the clinical combination study of carboplatin and anti-tumor agent eribulin mesylate (E7389) in human plasma," Journal of Chromatography B, 2008, 875:373-382.

Devriese et al., "Eribulin mesylate pharmacokinetics in patients with solid tumors receiving repeated oral ketoconazole," Invest New Drugs, 2013, 31:381-389.

Dong et al., "Tumor-associated B7-H1 promotes T-cell apoptosis: A potential mechanism of immune evasion," Natural Medicine, 2002, 8(8):793-800.

Dos Santos et al., "pH gradient loading of anthracyclines into cholesterol-five liposomes: enhancing drug loading rates through use of ethanol," Biochimica et Biophysica Acta, 2004, 1661:47-60.

Drummond, et al., Optimizing Liposomes for Delivery of Chemotherapeutic Agents to Solid Tumors, Pharmacological Reviews, 1999, 51(4):691-743.

Dybdal-Hargreaves et al., "Eribulin Mesylate: Mechanism of Action of a Unique Microtubule-Targeting Agent," Clinical Cancer Research, 2015, 21(11):2445-2452.

Eisai Co., Ltd., "FY2011 Financial Results Presentation," May 15, 2012, 68 pages (with English Translation).

(56) References Cited

OTHER PUBLICATIONS

Eisai Co., Ltd., "Halaven®," Code DI-T-HAL107, 6th edition, Feb. 2016, pp. 1-6 (with English Translation).
Eisai Co., Ltd., "Material Safety Data Sheet for Eribulin Mesylate," Oct. 2009, prepared by Greg Baker, 6 pages.
Eisai Co., Ltd., Eisai Public Relations Department, "Eisai and Merck Enter Collaboration to Explore Novel Combination Regimens of Anti-PD-1 Therapy with Multi-targeting RTK Inhibitor and Microtubule Dynamics in Multiple Types of Cancer," Mar. 4, 2015, retrieved from: URL<http//www.eisai.com/news/news201518.html>, 8 pages.
Eisai Co., Ltd., News Release No. 19-72, "Eisai to Present Abstracts on Oncology Products and Pipeline at ESMO 2019 Congress," dated Sep. 24, 2019, 3 pages.
Examiner's Answer in U.S. Appl. No. 14/061,426 dated Feb. 28, 2020, 3 pages.
Excerpted file history of U.S. Appl. No. 13/260,864: Issue fee payment (Apr. 9, 2018); Supplemental Notice of Allowability (dated Jan. 24, 2018); Corrected Filing Receipt (Jan. 17, 2018); Notice of Allowance and Issue Fee Due (dated Jan. 8, 2018).
Extended European Search Report in European Patent Application No. 10758754.5 dated Oct. 8, 2012, 10 pages.
Extended European Search Report in European Patent Application No. 10758755.2, dated Oct. 31, 2012 with corrected Written Opinion for EESR dated Dec. 19, 2012, 24 pages.
Extended European Search Report in European Patent Application No. 17789632.1, dated Nov. 27, 2019, 9 pages.
Fatouros et al., "Liposomes encapsulating prednisolone and prednisolone-cyclodextrin complexes: comparison of membrane integrity and drug release," European Journal of Pharmaceutical Sciences, 2001, 13:287-296.
Fenske et al., "Entrapment of small molecules and nucleic acid-based drugs in liposomes," Methods in Enzymology, 2005, 391:7-40.
Final and Non Final Office actions in U.S. Appl. No. 13/260,864, dated Nov. 10, 2015 and Oct. 14, 2015 respectively, 20 pages.
Final Rejection in Algerian Patent Application No. 110640, dated Aug. 18, 2013, 2 pages (with English Translation).
FormuMax Scientific Inc., "Doxoves-Liposome Doxorubicin Compared to Doxil," Doxoves-Liposomal Doxorubicin, 1995, 1-4, XP002684032, [Retrieved on Sep. 24, 2012], retrieved from: URL <www.liposomeexpert.com/categories/Drug-Loaded-Liposomes>.
Gao et al., "Overexpression of PD-L1 Significantly Associates with Tumor Aggressiveness and Postoperative Recurrence in Human Hepatocellular Carcinoma," Clin. Cancer Res., 2009, 15(3):971-979.
Ghebeh et al. "FOXP3$^+$T$_{regs}$ and B7-HI$^+$/PD-1$^+$T lymphocytes co-infiltrate the tumor tissues of high-risk breast cancer patients: Implication for immunotherapy," BMC Cancer, 2008, 8:57.
Ghebeh et al., "The B7-H1 (PD-L1) T Lymphocyte—Inhibitory Molecule is Expressed in Breast Cancer Patients with Infiltrating Ductal Carcinoma: Correlation with Important High-Risk Prognostic Factors," Neoplasia, 2006, 8(3):190-198.
Hagiwara et al., "Preparation and pharmaceutical evaluation of liposomes entrapping salicylic acid/γ-cyclodextrin conjugate," Chem. Pharm. Bull., 2006, 54(1):26-32.
Hamanishi et al., "Programmed cell death 1 ligand 1 and tumor-infiltrating CD8+ T lymphocytes are prognostic factors of human ovarian cancer," PNAS, 2007, 104(9):3360-3365.
Haran et al., "Transmembrane ammonium sulfate gradients in liposomes produce efficient and stable entrapment of amphipathic weak bases," Biochimica et Biophysica Acta. Biomembranes, 1993, 1151(2):201-215.
Hart et al., "Acid-catalyzed reactions of homohalichondrin B, a marine sponge-derived antitumor polyether macrolide," The Journal of Organic Chemistry, 1996, 61(8):2888-2890.
Hearing Notice in Indian Patent Application No. 6850/DELNP/2011, dated Aug. 17, 2017, 3 pages.

Hino et al., "Tumor Cell Expression of Programmed Cell Death-1 Ligand 1 Is a Prognostic Factor for Malignant Melanoma," Cancer, 2010, 116(7):1757-1766.
Inman et al., "PD-L1 (B7-H1) Expression by Urothelial Carcinoma of the Bladder and BCG-Induced Granulomata," Cancer, 2007, 109(8):1499-1505.
International Preliminary Report on Patentability in International Application No. PCT/US2016/020734, dated Sep. 5, 2017, 9 pages.
International Preliminary Report on Patentability in International Application No. PCT/US2017/056552, dated Apr. 25, 2019, 8 pages.
International Preliminary Report on Patentability in International Patent Application No. PCT/JP2017/016633, dated Oct. 30, 2018, 22 pages (with English Translation).
International Preliminary Report on Patentability in International Patent Application No. PCT/JP2010/055769, dated Oct. 4, 2011, 11 pages (with English Translation).
International Preliminary Report on Patentability in International Patent Application No. PCT/JP2010/055770, dated Nov. 15, 2011, 9 pages (with English Translation).
International Search Report and Written Opinion in International Patent Application No. PCT/US2017/056552, dated Jan. 2, 2018, 11 pages.
International Search Report in International Application No. PCT/JP2010/055770, dated Jun. 1, 2010, 2 pages.
International Search Report in International Application No. PCT/US2016/020734, dated Apr. 28, 2016, 7 pages.
International Search Report in International Patent Application No. PCT/JP2010/0055769, dated Jun. 8, 2010, 5 pages (with English Translation).
International Search Report in International Patent Application No. PCT/JP2017/016633, dated Jun. 6, 2017, 6 pages (with English Translation).
International Search Report in International Patent Application No. PCT/JP2018/020456, dated Aug. 28, 2018, 5 pages (with English Translation).
Intimation Notification in Indian Patent Application No. 6850/DELNP/2011, dated Aug. 23, 2018, 1 page.
Ishida et al., "Targeted delivery and triggered release of liposomal doxorubicin enhances cytotoxicity against human B lymphoma cell," Biochimica et Biophysica Acta, 2001, 1515:144-158.
IUPAC Goldbook, "Onium Compounds," Entry, [Retrieved on Mar. 9, 2016], retrieved from: URL<http://goldbook.iupac.org/O04291.html>, 2 pages.
Jordan et al., "The primary antimitotic mechanism of action of the synthetic halichondrin E7389 is suppression of microtubule growth," Molecular Cancer Therapeutics, 2005, 4(7):1086-1095.
Kazmi et al., "Real-world 1-year survival analysis of patients with metastatic breast cancer with liver or lung visceral metastasis treated with eribulin, gemcitabine," Poster Display, Abstract No. 366P, displayed Sep. 29, 2019, European Society for Medical Oncology (ESMO) 2019 Congress, Barcelona, Spain, 1 page.
Kikuchi, et al. "Liposome I—Method of Preparing and Testing," Cell Engineering, 1983, 2(9):1136-1149 (with English Translation).
Kim et al., "Multivescular liposomes containing cytarabine entrapped in the presence of hydrochloric acid for intracavitary chemotherapy," Cancer Treatment Reports, 1987, 71(7-8):705-711.
Kim et al., "Preparation of multivesicular liposomes," Biochimica et Biophysica Acta, 1983, 728:339-348.
Knollman et al., "Muscle-invasive urothelial bladder cancer: an update on systemic therapy," Therapeutic Advances in Urology, 2015, 7(6):312-330.
Kuznetsov et al., "Antiproliferative effects of halichondrin B analog eribulin mesylate (E7389) against paclitaxel-resistant human cancer cells in vitro," AACR-NCI-EORTC International Conference: Molecular Targets and Cancer Therapeutics. Abstract C58. Oct. 2007, 2 pages.
Lasic et al., "Gelation of liposome interior; A novel method for drug encapsulation," FEBS Lett., 1992, 312(2-3):255-258.
Lasic et al., "Transmembrane gradient driven phase transitions within vesicles: lessons for drug delivery," Biochimica et Biophysica Acta., 1995, 1239(2):145-156.

(56) References Cited

OTHER PUBLICATIONS

Liposomes, ed. Fude, CUI, Fifth Edition, People's Press of Hygiene, Mar. 2004, p. 386-394 (English explanation on Chinese Office Action in CN Appln. No. 201080014698.2 dated Oct. 24, 2012), 8 pages.
Loftsson T et al: "Solubilization and Stabilization of Drugs Through Cyclodextrin Complexation", Acta Pharmaceutica Nordica, 1991, 3(4):215-217.
Maeda, "EPR Effect," Kobunshi, 2000, 49(3):129 (with English Translation).
Maestrelli et al., "Effect of preparation technique on the properties of liposomes encapsulating ketoprofen—cyclodextrin complexes aimed for transdermal delivery," International Journal of Pharmaceutics, 2006, 312:53-60.
Matsumura et al., "A new concept for macromolecular therapeutics in cancer chemotherapy: mechanism of tumoritropic accumulation of proteins and the antitumor agent smancs," Cancer Research, 1986, 46:6387-6392.
Maurer-Spurej et al., "Factors influencing uptake and retention of amino-containing drugs in large unilamellar vesicles exhibiting transmembrane pH gradients," Biochimica et Biophysica Acta, 1999. 1416:1-10.
Mayer et al., "Uptake of adriamycin into large unilamellar vesicles in response to a pH gradient," Biochimica et Biophysica Acta, 1986, 857:123-126.
Memorandum in Response to Official Action in Israeli Patent Application No. 215059, dated Dec. 2, 2014, 58 pages.
Merck Sharp & Dohme Corp., "Highlights of Prescribing Information—KEYTRUDA® (pembrolizumab)," Label, Suppl. 8, revised Oct. 2016, FDA Ref. ID: 4003165, retrieved from: URL<https://www.accessdata.fda.gov/drugsatida_docs/label/2016/125514s008s0121b1.pdf>, 29 pages.
Merck Sharp & Dohme Corp., "Highlights of Prescribing Information—KEYTRUDA® (pembrolizumab)," Label, Suppl. 9, revised Aug. 2016, FDA Ref. ID: 3968676, retrieved from: URL<https://www.accessdata.fda.gov/drugsatida_docs/label/2016/125514s0091b1.pdf>, 26 pages.
Nakanishi et al., "Overexpression of B7-H1 (PD-L1) significantly associates with tumor grade and postoperative prognosis in human urothelial cancers," Cancer Immunol Immunother., 2007, 56:1173-1182.
Nanda et al., "Pembrolizumab in Patients With Advanced Triple-Negative Breast Cancer: Phase Ib. KEYNOTE-012 Study," Journal of Clinical Oncology, 2016, 34(21):2460-2467.
Nanda, "Pembrolizumab Shows Potential in Breast Cancer," Cancer Discovery, 2015, 5(2):100-101.
Narayan et al. "Novel second generation analogs of eribulin. Part III: blood—brain barrier permeability and in vivo activity in a brain tumor model," Bioorganic & Medicinal Chemistry Letters, 2011, 21(6):1639-1643.
Nippon Kayaku Co., Ltd., "Adriacin® for injection 10—Adriacin® for injection 50," Package Insert, revised Aug. 2011, 6 pages (with English Translation).
Nippon Kayaku Co., Ltd., "Exal® for injection 10 mg—Japanese Pharmacopeia (JP) Vinblastine Sulfate for Injection," Package Insert, revised Jul. 2011, 7 pages (with Partial Translation).
Nippon Kayaku Co., Ltd., "Oncovin® for injection 1 mg—Vincristine Sulfate Preparation," Package Insert, revised Aug. 2009, 7 pages (with Partial Translation).
Nippon Kayaku Co., Ltd., "Rozeus® Intravenous Solution 10 mg—Rozeus® Intravenous Solution 40 mg—Vinorelbine Ditartrate Intravenous Solution," Package Insert, revised Nov. 2009, 5 pages (with Partial Translation).
Nomi et al., "Clinical Significance and Therapeutic Potential of the Programmed Death-1 Ligand/Programmed Death-1 Pathway in Human Pancreatic Cancer," Clin. Cancer Res., 2007, 13(7):2151-2157.
Notice of Allowance in Australian Patent Application No. 2014200717, dated Feb. 13, 2016, 2 pages.
Notice of Allowance in Canadian Patent Application No. 2756811, dated Feb. 10, 2014, 1 page.
Notice of Allowance in Chilean Patent Application No. 2444-2011, dated Jul. 3, 2018, 8 pages (with English Translation).
Notice of Allowance in Chinese Patent Application No. 201080014698.2, dated Aug. 6, 2014, 4 pages (with English Translation).
Notice of Allowance in Colombian Patent Application No. 11-130828, dated Jan. 21, 2014, 12 pages (with English Translation).
Notice of Allowance in Indonesian Patent Application No. W00201103470 dated Apr. 20, 2017, 4 pages (with English Translation.
Notice of Allowance in Israeli Patent Application No. 215059, dated Nov. 25, 2015, 3 pages (with English Translation).
Notice of Allowance in Korean Patent Application No. 10-2011-7022860, dated Jan. 9, 2015, 4 pages (with English Translation).
Notice of Allowance in Mexican Patent Application No. MX/A/2011/009632, dated Oct. 14, 2014, 2 pages (with English Translation).
Notice of Allowance in New Zealand Patent Application No. 595212, dated Feb. 25, 2014, 1 page.
Notice of Allowance in Taiwanese Patent Application No. 099109838, dated Jan. 23, 2013, 5 pages (with English Translation).
Notice of Allowance in Ukrainian Patent Application No. a201111426, dated Jul. 23, 2013, 7 pages (with English Translation).
Notice of Final Rejection in Korean Patent Application No. 10-2011-7022860, dated Sep. 23, 2014, 5 pages (with English Translation).
Notice of Panel Decision in U.S. Appl. No. 14/061,426, dated Oct. 1, 2019, 2 pages.
Notice of Reason for Rejection in Japanese Patent Application No. 2011-507239, dated Feb. 27, 2014, 6 pages (with English Translation).
Notice of Reason for Rejection in Japanese Patent Application No. 2011-507240, dated Feb. 6, 2014, 7 pages (with English Translation).
Notice of Reason for Rejection in Japanese Patent Application No. 2014-092382, dated Jan. 28, 2015, 5 pages (with English Translation).
Notification of the Brazilian Patent and Trademark Office and Documents forwarded by ANVISA (Brazilian Health Surveillance Agency) for Brazilian Patent Application No. PI1014527-3, including transmittal letter (dated Jul. 31, 2019); Technical Written Opinion of Consent of a Patent Application of Pharmaceutical products and Processes (Jul. 18, 2019), supporting documents (Jul. 24, 2019), and "Documents Forwarded by ANVIA" (Sep. 5, 2019).
Observation Notification in Peruvian Patent Application No. 001798-2015, dated Feb. 12, 2020, 11 pages (with English Translation).
Observation Notification in Peruvian Patent Application No. 001798-2015, dated Oct. 16, 2019, 15 pages (with English Translation).
Office Action in Australian Patent Application No. 2010232347, dated May 11, 2012, 2 pages.
Office Action in Australian Patent Application No. 2014200717, dated Aug. 14, 2015, 2 pages.
Office Action in Brazilian Patent Application No. PI10145273, dated Mar. 30, 2020, 24 pages (with English Translation).
Office Action in Canadian Patent Application No. 2756811, dated Dec. 19, 2012, 4 pages.
Office Action in Canadian Patent Application No. 2756811, dated Jul. 17, 2013, 2 pages.
Office Action in Chilean Patent Application No. 2444-2011, dated Jan. 16, 2014, 6 pages (with English Translation).
Office Action in Chilean Patent Application No. 2444-2011, dated Jan. 21, 2015, 20 pages (with English Translation).
Office Action in Chilean Patent Application No. 2444-2011, dated Jul. 11, 2013, 19 pages (with English Translation).
Office Action in Chilean Patent Application No. 2444-2011, dated Dec. 18, 2015, 15 pages (with English Translation).
Office Action in Chinese Patent Application No. 201080014698.2 dated Oct. 24, 2012, 14 pages (with English Translation).
Office Action in Chinese Patent Application No. 201080014698.2, dated Aug. 8, 2013, 12 pages (with English Translation).
Office Action in Chinese Patent Application No. 201080014698.2, dated Mar. 28, 2014, 6 pages (with English Translation).

(56) References Cited

OTHER PUBLICATIONS

Office Action in Chinese Patent Application No. 201680025588.3, dated Jan. 6, 2020, 28 pages (with English Translation).
Office Action in Colombian Patent Application No. 11-130828, dated Aug. 8, 2013, 30 pages (with English Translation).
Office Action in Egyptian Patent Application No. PCT1637/2011, dated Jan. 14, 2016, 10 pages (with English Translation).
Office Action in European Patent Application No. 10758754.5, dated Jan. 24, 2014, 7 pages.
Office Action in European Patent Application No. 16710891.9, dated Aug. 13, 2019, 6 pages.
Office Action in European Patent Application No. 16710891.9, dated Mar. 31, 2020, 6 pages.
Office Action in European Patent Application No. 10758755.2, dated Jan. 24, 2014, 4 pages.
Office Action in Indian Patent Application No. 201747034283, dated Feb. 28, 2020, 7 pages (with English Translation).
Office Action in Indian Patent Application No. 6850DELNP2011, dated Nov. 10, 2016, 9 pages.
Office Action in Indonesian Patent Application No. W0020113470, dated Nov. 29, 2013, 7 pages (with English Translation).
Office Action in Israeli Patent Application No. 215059, dated Aug. 4, 2014, 3 pages (with English Translation).
Office Action in Japanese Patent Application No. 2017-546075, dated Jan. 7, 2020, 6 pages (with English Translation).
Office Action in Korean Patent Application No. 10-2011-7022860, dated Jul. 22, 2013, 20 pages (with English Translation).
Office Action in Korean Patent Application No. 10-2011-7022860, dated May 20, 2014, 11 pages (with English Translation).
Office Action in Korean Patent Application No. 10-2011-7022860, Notice of Preliminary Rejection, dated Dec. 28, 2012, 7 pages (with English Translation).
Office Action in Malaysian Patent Application No. PI2011004382, dated Apr. 15, 2013, 3 pages.
Office Action in Malaysian Patent Application No. PI2011004382, dated Sep. 30, 2016, 2 pages.
Office Action in Mexican Patent Application No. MX/a/2011/009632, dated Apr. 22, 2013, 12 pages (with English Translation).
Office Action in Mexican Patent Application No. MX/a/2011/009632, dated Aug. 7, 2012, 6 pages (with English Translation).
Office Action in Mexican Patent Application No. MX/a/2011/009632, dated Jan. 17, 2014, 6 pages (with English Translation).
Office Action in New Zealand Patent Application No. 595212, dated Aug. 14, 2012, 1 page.
Office Action in Peruvian Patent Application No. 001735-2011/DIN, dated Jan. 9, 2014, 2 pages (with English Translation).
Office Action in Peruvian Patent Application No. 001735-2011/DIN, dated Nov. 23, 2012, 15 pages (with English Translation).
Office Action in Peruvian Patent Application No. 001735-2011/DIN, dated Sep. 29, 2014, 7 pages (with English Translation).
Office Action in Philippine Patent Application No. 1/2011/501838, dated Jun. 4, 2015, 1 page.
Office Action in Philippine Patent Application No. 1-2011-501838, dated Aug. 8, 2013, 1 page.
Office Action in Philippine Patent Application No. 12011-501838, dated Sep. 17, 2014, 2 pages.
Office Action in Russian Patent Application No. 2017132877, dated Aug. 29, 2019, 12 pages (with English Translation).
Office Action in Russian Patent Application No. 2017132877, dated Jan. 27, 2020, 8 pages (with English Translation).
Office Action in Russian Patent Application. No. 2011139715/20(059371), dated Nov. 28, 2011, (with partial English Translation), with Applicant Response filed on Jan. 30, 2012, 4 pages.
Office Action in Taiwanese Patent Application No. 099109838, dated Jun. 22, 2012, 9 pages (with English Translation).
Office Action in U.S. Appl. No. 13/260,864, dated Feb. 3, 2017, 11 pages.
Office Action in U.S. Appl. No. 13/260,864, dated Jul. 13, 2015, 11 pages.
Office Action in U.S. Appl. No. 13/260,864, dated Jun. 27, 2016, 10 pages.
Office Action in U.S. Appl. No. 13/260,864, dated Mar. 10, 2014, 8 pages.
Office Action in U.S. Appl. No. 13/260,864, dated Sep. 26, 2014, 15 pages.
Office Action in U.S. Appl. No. 13/260,872, dated Apr. 24, 2013, 24 pages.
Office Action in U.S. Appl. No. 13/260,872, dated Aug. 1, 2012, 17 pages.
Office Action in U.S. Appl. No. 14/061,426 dated Oct. 30, 2017, 17 pages.
Office Action in U.S. Appl. No. 14/061,426, dated May 30, 2019, 17 pages.
Office Action in U.S. Appl. No. 14/061,426, dated May 31, 2017, 39 pages.
Office Action in U.S. Appl. No. 14/061,426, dated Nov. 19, 2018, 23 pages.
Office Action in U.S. Appl. No. 14/061,426, dated Sep. 24, 2015, 17 pages.
Office Action in U.S. Appl. No. 14/061,426, dated Mar. 18, 2016, 24 pages.
Office Action in U.S. Appl. No. 15/554,540, dated Jan. 2, 2020, 15 pages.
Office Action in U.S. Appl. No. 15/554,540, dated Mar. 22, 2020, 27 pages.
Office Action in U.S. Appl. No. 16/090,360, dated Mar. 11, 2020, 9 pages.
Office Action in U.S. Appl. No. 16/090,360, dated Oct. 21, 2019, 8 pages.
Office Action in Vietnamese Patent Application No. 1-2011-02950, dated Aug. 16, 2013, 3 pages (with English Translation).
Office Action in Vietnamese Patent Application No. 10-2011-02950, dated Mar. 31, 2016, 3 pages (with English Translation).
Official Decision in Egyptian Patent Application No. PCT1637/2011, dated Jan. 3, 2017, 8 pages (with English Translation).
Official Notification in Peruvian Patent Application No. 001735-2011/DIN, dated Jul. 16, 2015, 28 pages (with English Translation).
Official Notification in Vietnamese Patent Application No. 1-2011-02950, dated Jan. 24, 2017, 2 pages (with English Translation).
Ohigashi et al., "Clinical Significance of Programmed Death-1 Ligand-1 and Programmed Death-1 Ligand-2 Expression in Human Esophageal Cancer," Clin. Cancer Res., 2005, 11(8):2947-2953.
Okouneva et al., "Inhibition of centromere dynamics by eribulin (E7389) during mitotic metaphase," Molecular Cancer Therapeutics, 2008, 7(7):2003-2011.
Opposition in Colombian Patent Application No. 11-130828, dated Apr. 30, 2012, 14 pages (with English Translation).
Opposition in Colombian Patent Application No. 11-130828, dated Jul. 25, 2012, 14 pages (with English Translation).
Opposition in Peruvian Patent Application No. 001735-2011/DIN, dated Jan. 20, 2015, 25 pages (with English Translation).
Opposition in Peruvian Patent Application No. 001798-2015, dated Jan. 25, 2016, 18 pages (with English Translation).
Pardoll, "The blockade of immune checkpoints in cancer immunotherapy," Nature Reviews Cancer, 2012, 12:252-264.
Peleg-Shulman et al., "Characterization of sterically stabilized cisplatin liposomes by nuclear magnetic resonance," Biochimica et Biophysica, 2001, 1510(1-2): 278-291.
Petition in Japanese Patent Application No. 2014-092382, dated Dec. 26, 2014, 9 pages (with English Translation).
Piel et al., "Betamethasone-in-cyclodextrin-in-liposome: The effect of cyclodextrins on encapsulation efficiency and release kinetics," International Journal of Pharmaceutics, 2006, 312:75-82.
Poujol et al., "Stability of the ready-to use solutions of eribulin for intravenous infusion," Annales pharmaceutiques françaises, 2012, 70(5):249-255.
Preliminary Amendment filed in Japanese Patent Application No. 2014-092382 dated May 28, 2014, 4 pages (with English Translation).
Preliminary Conclusion in Ukrainian Patent Application No. a201111426, dated Apr. 8, 2013, 8 pages (with English Translation).

(56) References Cited

OTHER PUBLICATIONS

Rajora et al., "Impact of the Enhanced Permeability and Retention (EPR) Effect and Cathepsins Levels on the Activity of Polymer-Drug Conjugates," Polymers, 2014, 6:2186-2220.
Resolution in Peruvian Patent Application No. 001735-2011/DIN, dated Nov. 30, 2015, 50 pages (with English Translation).
Response filed in New Zealand Patent Application No. 595212, dated Feb. 7, 2014, 4 pages.
Response filed in Algerian Patent Application No. 110640, dated Aug. 29, 2016, 26 pages (with English Translation).
Response filed in Australian Patent Application No. 2014200717, dated Dec. 22, 2015, 7 pages.
Response filed in Canadian Patent Application No. 2756811, dated Jan. 16, 2014, 15 pages.
Response filed in Canadian Patent Application No. 2756811, dated Jun. 19, 2013 to the Office Action dated Dec. 19, 2012, 21 pages.
Response filed in Chilean Patent Application No. 2444-2011, dated Apr. 16, 2015 to the Office Action dated Jan. 21, 2015, 142 pages (with English Translation).
Response filed in Chilean Patent Application No. 2444-2011, dated Jun. 5, 2015, 8 pages (with English Translation).
Response filed in Chilean Patent Application No. 2444-2011, dated Mar. 11, 2014 to the Opposition dated Jan. 2014, 6 pages (with English Translation).
Response filed in Chilean Patent Application No. 2444-2011, dated Mar. 14, 2016 to the Office Action dated Dec. 11, 2015, 12 pages (with English Translation).
Response filed in Chinese Patent Application No. 201080014698.2, dated Dec. 23, 2013 to Office Action dated Aug. 8, 2013, 14 pages (with English Translation).
Response filed in Chinese Patent Application No. 201080014698.2, dated May 29, 2014 to the Office Action dated Mar. 28, 2014, 13 pages (with English Translation).
Response filed in Colombian Patent Application No. 11-130828, dated Dec. 2, 2013, 24 pages (with English Translation).
Response filed in Colombian Patent Application No. 11-130828, dated Jan. 14, 2013 to the Opposition dated Jul. 25, 2012, 10 pages (with English Translation).
Response filed in Egyptian Patent Application No. PCT1637/2011, dated Apr. 18, 2016, 20 pages (with English Translation).
Response filed in Egyptian Patent Application No. PCT1637/2011, dated Mar. 30, 2017, to the Office Decision dated Jan. 3, 2017, 21 pages (with English Translation).
Response filed in European Patent Application No. 10758754.5, dated Aug. 1, 2014 to Communication to Art 94(3) dated Jan. 24, 2014, 15 pages.
Response filed in European Patent Application No. 10758754.5, dated May 3, 2013 to the Office Action dated Oct. 25, 2012 and to the EESR dated Oct. 8, 2012 , 8 pages.
Response filed in European Patent Application No. 10758755.2, dated Jun. 3, 2014 to the Office Action dated Jan. 24, 2014, 82 pages.
Response filed in European Patent Application No. 10758755.5, dated May 29, 2013 to the EESR dated Nov. 19, 2012, 10 pages.
Response filed in European Patent Application No. 17789632.1, dated Jun. 24, 2020, to the Communication Pursuant to Rules 70(2)/70a(2) EPC dated Dec. 17, 2019, including Amendment, 5 pages.
Response filed in Indian Patent Application No. 6850/DELNP/2011, dated Oct. 3, 2017 to Result for Hearing Notice, including Amendment, 320 pages.
Response filed in Indonesian Patent Application No. W00201103470, dated Mar. 25, 2014, 7 pages (with English Translation).
Response filed in Japanese Patent Application No. 2011-507239, dated Apr. 28, 2014 to the Office Action dated Feb. 27, 2014, 5 pages (with English Translation).
Response filed in Japanese Patent Application No. 2011-507240, dated Apr. 7, 2014 to the Office Action dated Feb. 6, 2014, 26 pages (with English Translation).
Response filed in Japanese Patent Application No. 2014-092382, dated Mar. 27, 2015 to the Office Action dated Jan. 28, 2015, including Amendment and argument, 13 pages (with English Translation).
Response filed in Korean Patent Application No. 10-2011-7022860, dated Dec. 24, 2014 to the Notice of Final Rejection dated Sep. 23, 2014, 18 pages (with English Translation).
Response filed in Korean Patent Application No. 10-2011-7022860, dated Feb. 28, 2013 to the Office Action dated Dec. 28, 2012, 31 pages (with English Translation).
Response filed in Korean Patent Application No. 10-2011-7022860, dated Jan. 22, 2014 to the Office Action dated Jul. 22, 2013, 31 pages (with English Translation).
Response filed in Korean Patent Application No. 10-2011-7022860, dated Jul. 18, 2014 to the Office Action dated May 20, 2014, including amendment, 15 pages (with English Translation).
Response filed in Malaysian Patent Application No. PI2011004382, dated Jun. 14, 2013 to Substantive Examination Adverse Report dated Apr. 15, 2013, 6 pages.
Response filed in Mexican Patent Application No. MX/a/2011/009632 dated Jan. 7, 2013, to the Office Action dated Aug. 7, 2012, 17 pages (with English Translation).
Response filed in Mexican Patent Application No. MX/a/2011/009632, dated Jun. 17, 2014, 22 pages (with English Translation).
Response filed in Mexican Patent Application No. MX/a/2011/009632, dated Sep. 18, 2013 to the Office Action dated Apr. 22, 2013, 20 pages (with English Translation).
Response filed in Peruvian Patent Application No. 001735-2011/DIN, dated Aug. 12, 2015 18 pages (with English Translation).
Response filed in Peruvian Patent Application No. 001735-2011/DIN, dated Jan. 20, 2014, 2 pages (with English Translation).
Response filed in Peruvian Patent Application No. 001735-2011/DIN, dated Jan. 21, 2013 to the Peruvian Opposition dated Nov. 23, 2012, 5 pages (with English Translation).
Response filed in Peruvian Patent Application No. 001735-2011/DIN, dated May 20, 2015, 48 pages (with English Translation).
Response filed in Peruvian Patent Application No. 001798-2015, dated Jan. 4, 2020 to the Observation dated Oct. 16, 2019, 12 pages (with English Translation).
Response filed in Peruvian Patent Application No. 1798-2015, dated Apr. 28, 2016, 10 pages (with English Translation).
Response filed in Peruvian Patent Application No. 001735-2011/DIN, dated Oct. 27, 2014 to Office Action dated Sep. 29, 2014, 3 pages.
Response filed in Philippine Patent Application No. 1-2011-501838, dated Jul. 24, 2015, 13 pages.
Response filed in Philippine Patent Application No. 1-2011-501838, dated Nov. 11, 2014, submitting English translation of JP 5551683 B2 in reply to Paper No. 9 mailed Sep. 17, 2014, 59 pages.
Response filed in Philippine Patent Application No. 1-2011-501838, dated Sep. 18, 2015 to the Office Action dated Aug. 27, 2015, 1 page.
Response filed in Philippine Patent Application No. 1-2011-501838, dated Sep. 30, 2013 to the Office Action dated Aug. 8, 2013, 1 page.
Response filed in Russian Patent Application No. 2011139715/20(059371), dated Jan. 30, 2012, 12 pages (with partial English Translation).
Response filed in Ukrainian Patent Application No. a201111426, dated Jun. 11, 2013, to the Office Action (Preliminary Conclusion on Non-patentability) , 9 pages (with English Translation).
Response filed in U.S. Appl. No. 13/260,864, dated Aug. 1, 2017, including Request for Continued Examination, 51 pages.
Response filed in U.S. Appl. No. 13/260,864, dated Dec. 22, 2016, including Amendment, 22 pages.
Response filed in U.S. Appl. No. 13/260,864, dated Mar. 9, 2016 to the Final Office Action dated Nov. 20, 2015, including Amendment, 16 pages.
Response filed in U.S. Appl. No. 13/260,864, dated May 26, 2015, including Supplemental Amendment, Statement of Substance of Interview, and Applicant-Initiated Interview Summary dated Apr. 27, 2015, 17 pages.
Response filed in U.S. Appl. No. 13/260,864, dated Oct. 13, 2015, to the Non-Final Office Action dated Jul. 13, 2015, 17 pages.

(56) References Cited

OTHER PUBLICATIONS

Response filed in U.S. Appl. No. 13/260,864, including Amendment and Request for Continued Examination, dated Mar. 23, 2015, 23 pages.
Response filed in U.S. Appl. No. 13/260,864, including amendment, dated Sep. 9, 2014, 19 pages.
Response filed in U.S. Appl. No. 13/260,872, including amendments and two exhibits, dated Feb. 1, 2013, 167 pages.
Response filed in U.S. Appl. No. 14/061,426, dated Jul. 15, 2015, 4 pages.
Response filed in U.S. Appl. No. 14/061,426, dated Apr. 25, 2018, including Amendment and RCE, 32 pages.
Response filed in U.S. Appl. No. 14/061,426, dated Aug. 26, 2019 to the Final Office Action dated May 30, 2019, 7 pages.
Response filed in U.S. Appl. No. 14/061,426, dated Aug. 30, 2017 to the Office Action dated May 31, 2017, 48 pages.
Response filed in U.S. Appl. No. 14/061,426, dated Dec. 22, 2015, 125 pages.
Response filed in U.S. Appl. No. 14/061,426, dated Dec. 23, 2019 to the Final Office Action dated May 30, 2019, 50 pages.
Response filed in U.S. Appl. No. 14/061,426, dated Feb. 7, 2019, to the Office Action dated Nov. 19, 2018, 23 pages.
Response filed in U.S. Appl. No. 14/061,426, dated Mar. 17, 2020 to the Examiner's Answer dated Feb. 28, 2020, 3 pages.
Response filed in U.S. Appl. No. 14/061,426, dated Oct. 24, 2013, including Preliminary Amendment, 1 page.
Response filed in U.S. Appl. No. 14/061,426, dated Sep. 19, 2016, including RCE, ADS, and Amendment, 70 pages.
Response filed in U.S. Appl. No. 16/090,360, dated Jan. 10, 2020 to the Office Action dated Oct. 21, 2019, 9 pages.
Response filed in Vietnamese Patent Application No. 1-2011-02950, dated Dec. 13, 2013, 8 pages (with English Translation).
Response filed in Vietnamese Patent Application No. 1-2011-02950, dated May 30, 2016, 4 pages (with English Translation).
Response in Taiwanese Patent Application No. 099109838, dated Dec. 27, 2012 to the Office Action dated Jun. 22, 2012, 21 pages (with English Translation).
Restriction in U.S. Appl. No. 14/061,426, dated May 15, 2015, 7 pages.
Satsuka, "Recent evolution of liposome application," NTS, 2005, 16 pages (with English Translation).
Schöffski et al., "Activity of eribulin mesylate in patients with soft-tissue sarcoma: a phase 2 study in four independent histological subtypes," The Lancet Oncology, 2011, 12:1045-1052.
Sharpe et al., "The function of programmed cell death 1 and its ligands in regulating autoimmunity and infection," Nature Immunology, 2007, 8(3):239-245.
Shimauchi et al., "Augmented expression of programmed death-1 in both neoplastic and non-neoplastic CD4+ T-cells in adult T-cell leukemia/lymphoma," Int. J. Cancer, 2007, 121:2585-2590.
Takahashi et al., "One-year follow-up results of eribulin for soft-tissue sarcoma including rare subtypes in a real-world observational study in Japan," Poster Display, Abstract No. 1683P displayed Sep. 28, 2019, European Society for Medical Oncology (ESMO) 2019 Congress, Barcelona, Spain, 1 page.
TheFreeDictionary.com [Online], "Residues," [Retrieved on Jul. 15, 2014], retrieved from: URL<http://medical-dictionary.thefreedictionary.com/p/Residues>, 2 pages.
Thompson et al., "PD-1 is expressed by tumor-infiltrating immune cells and is associated with poor outcome for patients with renal cell carcinoma," Clin. Cancer Res., 2007, 13(6):1757-1761.
Thompson et al., "Significance of B7-H1 Overexpression in Kidney Cancer," Clinical Genitourinary Cancer, 2006, 5(3):206-211.
Tolaney et al., "Phase 1b/2 study to evaluate eribulin mesylate in combination with pembrolizumab in patients with metastatic triple-negative breast cancer," [Abstract No. 177], Eur. J. Cancer, 2017, 72:S16.
Twelves et al., "Efficacy of eribulin in women with metastatic breast cancer: a pooled analysis of two phase 3 studies," Breast Cancer Res. Treat., 2014, 148:553-561.
Voluntary Amendment filed in Cambodian Patent Application No. KH/P/10/00097, dated Jul. 7, 2016, 4 pages.
Wang et al. "Eribulin mesilate," Drugs of the Future, 2007, 32(8): 681-698.
Whatsthedose.com [online], "NORMOSOL®—R pH 7.4—Packaging Insert," Hospira, Inc., revised Oct. 2006, [Retrieved on Jul. 20, 2012], retrieved from: URL<http://whatsthedose.com/sp1/0409-7670.html>, 10 pages.
Written Opinion in International Patent Application No. PCT/US2016/020734, dated Apr. 28, 2016, 8 pages.
Written Opinion in International Patent Application No. PCT/JP2018/020456, dated Aug. 28, 2018, 15 pages (with English Translation).
Written Opinion in Singaporean Patent Application No. 11201706872S, dated Jun. 27, 2018, 7 pages.
Written Opinion in Singaporean Patent Application No. 11201706872S, dated Nov. 5, 2019, 10 pages.
Yamamoto et al., "Phase 1 study of liposomal formulation of eribulin (E7389-LF) in Patients with Advanced Solid Tumors: Primary Results of the Dose-Escalation Part," Poster Display, Abstract No. 348P, displayed Sep. 29, 2019, European Society for Medical Oncology (ESMO) 2019 Congress, Barcelona, Spain, 1 page.
Yang et al., "PD-L1 Interaction Contributes to the Functional Suppression of T-Cell Responses to Human Uveal Melanoma Cells in Vitro," Invest. Ophthalmol Vis. Sci., 2008, 49(6):2518-2525.
Yi et al., "Biomarkers for predicting efficacy of PD-1/PD-L1 inhibitors," Molecular Cancer, 2018, 17:129.
Yin et al., "Enhanced Permeability and Retention (EPR) Effect Based Tumor Targeting: The Concept, Application and Prospect," JSM Clinical Oncology and Research, 2014, 2(1):1010.
Yu et.al., "Characterization of the pharmacokinetics of a liposomal formulation of eribulin mesylate (E7389) in mice," International Journal of Pharmaceutics, 2013, 443:9-16.
Zibelman et al., "Checkpoint Inhibitors and Urothelial Carcinoma: The Translational Paradigm," Oncology, 2016, 30(2):160-162.
Zucker et al., "Liposome drugs' loading efficiency: A working model based on loading conditions and drug's physicochemical properties," Journal of Controlled Release, 2009, 139(1):73-80.
Furnishing of Prescribed Information and Voluntary Amendment and Payment of Fee for Grant in Singaporean Patent Application No. 201106388-0, dated Mar. 26, 2014, 17 pages.
Patent Certificate for Australian Patent No. 2014200717, granted on Jun. 9, 2016, 1 page.
Patent Certificate for Bruneian Patent No. RE-R-2017-0029, granted on Jul. 6, 2017, 1 page.
Patent Certificate for Canadian Patent No. 2,756,811, granted on Sep. 23, 2014, 2 pages.
Patent Certificate for Chilean Patent No. 56.288, granted on Jul. 3, 2018, 2 pages (with English Translation).
Patent Certificate for Chinese Patent No. ZL201080014698.2, granted on Oct. 29, 2014, 3 pages (with English Translation).
Patent Certificate for Colombian Patent No. 4584, granted on Jan. 17, 2014, 2 pages (with English Translation).
Patent Certificate for European Patent No. 2415464, granted on May 10, 2017, 1 page.
Patent Certificate for European Patent No. 2415470, granted on Jul. 6, 2016, 1 page.
Patent Certificate for Hong Kong Patent No. HK1165707, granted on Jul. 7, 2017, 2 pages.
Patent Certificate for Indian Patent No. 300213, dated Aug. 23, 2018, 1 page.
Patent Certificate for Indonesian Patent No. IDP000045351, granted on Apr. 20, 2017, 66 pages (with English Translation).
Patent Certificate for Israeli Patent No. 215059, granted on Jul. 1, 2016, 4 pages.
Patent Certificate for Japanese Patent No. 5551683, granted on May 30, 2014, 4 pages (with English Translation).
Patent Certificate for Japanese Patent No. 5622719, granted on Oct. 3, 2014, 4 pages (with English Translation).
Patent Certificate for Japanese Patent No. 5770366, granted on Jul. 3, 2015, 4 pages (with English Translation).
Patent Certificate for Korean Patent No. 10-1495951, granted on Feb. 16, 2015, 4 pages (with English Translation).

(56) References Cited

OTHER PUBLICATIONS

Patent Certificate for Malaysian Patent No. MY-160203-A, granted on Feb. 28, 2017, 4 pages.
Patent Certificate for Mexican Patent No. 326330, granted on Dec. 15, 2014, 2 pages (with English Translation).
Patent Certificate for Moroccan Patent No. 33127, granted on Mar. 1, 2012, 3 pages (with English Translation).
Patent Certificate for New Zealand Patent No. 595212, granted on Jun. 4, 2014, 1 page.
Patent Certificate for Philippine Patent No. 1-2011-501838, granted on Nov. 25, 2015, 69 pages.
Patent Certificate for Russian Patent No. 2476216, granted on Feb. 27, 2013, 44 pages (with English Translation).
Patent Certificate for Singaporean Patent No. 174255, granted on Apr. 15, 2014, 2 pages.
Patent Certificate for South African Patent No. 2011-06535, granted on May 30, 2012, 3 pages.
Patent Certificate for Sri Lankan Patent No. 16427, granted on Aug. 6, 2014, 3 pages.
Patent Certificate for Taiwanese Patent No. I392519, granted on Apr. 11, 2013, 3 pages (with English Translation).
Patent Certificate for Ukrainian Patent No. 103794, granted on Nov. 25, 2013, 32 pages (with English Translation).
Patent Certificate for U.S. Pat. No. 9,968,583, granted on May 15, 2018, 34 pages.
Patent Certificate for Vietnamese Patent No. 17167, granted on Jul. 4, 2017, 58 pages (with English Translation).
Request for Examination in Brazilian Patent Application No. PI10145273, dated Mar. 30, 2013, 6 pages (with English Translation).
Request for Examination in Chinese Patent Application No. 201080014698.2, dated Sep. 29, 2011, 5 pages (with English Translation).
Request for Examination in Chinese Patent Application No. 201880024121.6, dated Oct. 9, 2019, 2 pages (with English Translation).
Request for Examination in Colombian Patent Application No. 11-130828, dated Jul. 17, 2012, 2 pages (with English Translation).
Request for Examination in Egyptian Patent Application No. PCT1637-2011, dated Oct. 3, 2011, 1 page (with English Translation).
Request for Examination in Indian Patent Application No. 6850-DELNP-2011, dated Sep. 7, 2011, 6 pages.
Request for Examination in Indonesian Patent Application No. W-00201103470, dated Sep. 29, 2011, 2 pages (with English Translation).
Request for Examination in Japanese Patent Application No. 2011-507239, dated Jan. 10, 2013, 2 pages (with English Translation).
Request for Examination in Japanese Patent Application No. 2011-507240, dated Jan. 10, 2013, 2 pages (with English Translation).
Request for Examination in Japanese Patent Application No. 2014-92382, dated May 28, 2014, 2 pages (with English Translation).
Request for Examination in Japanese Patent Application No. 2018-514683, dated Apr. 17, 2020, 2 pages (with English Translation).
Request for Examination in Malaysian Patent Application No. PI2011004382, dated Sep. 15, 2011, 1 page.
Request for Examination in Russian Patent Application No. 2011139715, dated Sep. 29, 2011, 2 pages (with English Translation).
Request for Examination in Taiwanese Patent Application No. 147388, dated Mar. 30, 2013, 9 pages (with English Translation).
Request for Examination in Ukrainian Patent Application No. a201111426, dated Sep. 27, 2011, 2 pages (with English Translation).
Request for Examination in Vietnamese Patent Application No. 1-2011-02950, dated Oct. 31, 2011, 6 pages (with English Translation).
Response filed in Brazilian Patent Application No. PI10145273, dated Jul. 2, 2020, to the Office Action dated Mar. 30, 3030, 80 pages (with English Translation).
Notice of Abandonment in U.S. Appl. No. 13/260,872, dated Dec. 3, 2013, 2 pages.

Notice of Allowance in Brazilian Patent Application No. PI10145273, dated Oct. 20, 2020, 2 pages (with English Translation).
Office Action in Chinese Patent Application No. 201680025588.3, dated Jul. 7, 2020, 29 pages (with English Translation).
Office Action in Japanese Patent Application No. 2017-546075, dated Jul. 21, 2020, 6 page (with English Translation).
Communication pursuant to Article 94(3) EPC in European Patent Application No. 16710891.9, dated Nov. 16, 2020, 24 pages.
Letters Patent for the Brazilian Patent No. PI 1014527-3, granted on Nov. 24, 2020, 70 pages (with English Translation).
Notice of Allowance in U.S. Appl. No. 15/554,540, dated Nov. 4, 2020, 7 pages.
Notice of Intention to Refuse Patent Application in Singaporean Patent Application No. 11201706872S, dated Nov. 19, 2020, 11 pages.
Office Action in Mexican Patent Application No. MX/a/2017/011206, dated Nov. 24, 2020, 8 pages (with Partial Translation).
Office Action in U.S. Appl. No. 15/554,540, dated Aug. 11, 2020, 7 pages.
Response filed in U.S. Appl. No. 15/554,540, dated May 4, 2020, 23 pages.
Response filed in U.S. Appl. No. 15/554,540, dated Oct. 13, 2020, 7 pages.
Response filed in U.S. Appl. No. 15/554,540, dated Sep. 23, 2019, 38 pages.
Schmidt et al., "Assessment of Clinical Activity of PD-1 Checkpoint Inhibitor Combination Therapies Reported in Clinical Trials," JAMA Network Open. Feb. 2020, 3(2):e1920833.
Office Action in U.S. Appl. No. 17/067,302, dated Dec. 30, 2020, 58 pages.
ClinicalTrials.gov [online], "A Study of E7389 Liposomal Formulation (E7389-LF) Plus Nivolumab in Participants with Solid Tumor, History of Changes for Study: NCT04078295," Sep. 2019, retrieved from: URL<https://clinicaltrials.gov/ct2/history/NCT04078295?V_1=View#StudyPageTop, Sep. 2, 2019>, 4 pages.
Eisai Co., Ltd., News Release No. 20-54, "Eisai to present abstracts on oncology products and pipeline at ESMO Virtual Congress 2020," dated Sep. 11, 2020, 3 pages.
Eisai Co., Ltd., News Release No. 20-56, "Eisai presents latest data of phase I clinical trial on liposomal formulation of anti-cancer agent Halaven® (Eribulin) at ESMO Virtual Congress 2020," dated Sep. 18, 2020, 3 pages.
Iwasa et al., "Effect of infusion rate, premedication, and prophylactic peg-filgrastim treatment on the safety of the liposomal formulation of eribulin (E7389-LF): Results from the expansion part of a phase 1 study," Abstract 583P, Sep. 17, 2020, the European Society for Medical Oncology (ESMO) Virtual Congress, Sep. 19-21, 2020, Annals of Oncology (2020) 31 (suppl_4): S462-S504, 10.1016/annonc/annonc271, NPL277, 8 pages.
Iwasa et al., "Effect of infusion rate, premedication, and prophylactic peg-filgrastim treatment on the safety of the liposomal formulation of eribulin (E7389-LF): Results from the expansion part of a phase 1 study," E-poster for Abstract 583P, presented at the European Society for Medical Oncology (ESMO) Virtual Congress, Sep. 19-21, 2020, Annals of Oncology (2020) 31 (suppl_4):S462-S504, 10.1016/annonc/anonc271, 1 page.
Letters Patent for Patent No. 10271 in Algerian Patent Application No. 110640, dated Sep. 13, 2020, 4 pages (with English Translation).
Office Action in Brazilian Patent Application No. PI10145273, dated Jul. 14, 2020, 9 pages (with English Translation).
Office Action in U.S. Appl. No. 14/061,426, dated Sep. 1, 2020, 21 pages.
Office Action in U.S. Appl. No. 16/090,360, dated Oct. 2, 2020, 31 pages.
Patent Certificate for Bruneian Patent No. RE-R-2017-0029, granted on Jul. 4, 2017, 1 page.
Patent Certificate for Japanese Patent No. 5770336, granted on Jul. 3, 2015, 4 pages (with English Translation).
PCT International Search Report in International Patent Application No. PCT/JP2020/028663, dated Sep. 24, 2020, 20 pages (with English Translation).

(56) References Cited

OTHER PUBLICATIONS

Request for Examination in Brazilian Patent Application No. PI10145273, dated Dec. 27, 2011, 6 pages (with English Translation).

Request for Examination in Ukrainian Patent Application No. a201111426, dated Feb. 1, 2013, 2 pages (with English Translation).

Response filed in Brazilian Patent Application No. PI10145273, dated Jul. 2, 2020, to the Office Action dated Mar. 30, 2020, 80 pages (with English Translation).

Response filed in Brazilian Patent Application No. PI10145273, dated Oct. 6, 2020, to the Office Action dated Jul. 14, 2020, 20 pages (with English Translation).

Response filed in Peruvian Patent Application No. 001798-2015, dated Jul. 23, 2020, 15 pages (with English Translation).

Response filed in U.S. Appl. No. 16/090,360, dated Jul. 13, 2020, to the Final Office Action dated Mar. 11, 2020, 9 pages.

Tamura et al., "Phase 1 study of the liposomal formulation of eribulin (E7389-LF): Results from the HER2-negative breast cancer expansion part," Eposter for Abstract 346P, presented at the European Society for Medical Oncology (ESMO) Virtual Congress, Sep. 19-21, 2020, Annals of Oncology (2020) 31(suppl_4):S348-S395, 10.1016/annonc/annonc268, 1 page.

Tamura et al., "Phase 1 study of the liposomal formulation of eribulin (E7389-LF): Results from the HER2-negative breast cancer expansion," Abstract 346P, dated Sep. 17, 2020, the European Society for Medical Oncology (ESMO) Virtual Congress, Sep. 19-21, 2020, Annals of Oncology (2020) 31(suppl_4):S348-S395, 10.1016/annonc/annonc268, 7 pages.

Tolaney et al., "Abstract PD6-13: Phase 1b/2 study to evaluate eribulin mesylate in combination with pembrolizumab in patients with metastatic triple-negative breast cancer," Cancer Research, Feb. 2018, vol. 78, 4 pages.

Official Decision in Egyptian Patent Application No. PCT1637/2011, dated Dec. 29, 2020, 10 pages (with English Translation).

Response filed in U.S. Appl. No. 14/061,426, dated Feb. 26, 2021, 27 pages.

Response filed in U.S. Appl. No. 16/090,360, dated Feb. 26, 2021, 11 pages.

Response filed in Egyptian Patent Application No. PCT1637/2011, dated Mar. 25, 2021, 17 pages (with English Translation).

Response filed in U.S. Appl. No. 17/067,302, dated Mar. 19, 2021, 15 pages.

Masuda et al., "Phase 1 Expansion Study of Liposomal Formulation of Eribulin (E7389-LF) for solid Tumors: Focus on Breast Cancer," Presentation, The Japanese Society of Medical Oncology Annual Meeting, Feb. 21, 201, 17 pages.

Office Action in Japanese Patent Application No. 2018-514683, dated Apr. 7, 2021, 9 pages (with English Translation).

Request for Continued Examination in U.S. Appl. No. 17/067,302, dated Apr. 12, 2021, 1 page.

Final Office Action in U.S. Appl. No. 14/061,426, dated Mar. 26, 2021, 19 pages.

Final Office Action in U.S. Appl. No. 16/090,360, dated Apr. 2, 2021, 7 pages.

Masuda et al., "Phase 1 Expansion Study of Liposomal Formulation of Eribulin (E73389-LF) for Solid Tumors: Focus on Breast Cancer," The Japanese Society of Medical Oncology Annual Meeting, Feb. 10, 2021, p. 670.

Masuda et al., "Phase 1 Expansion Study of Lipsomal Formulation of Eribulin (E7389-LF) for Solid Tumors: Focus on Breast Cancer," Presentation, The Japanese Society of Medical Oncology Annual Meeting, Feb. 10, 2021, 17 pages.

Notice of Allowance in U.S. Appl. No. 17/067,302, dated Mar. 31, 2021, 8 pages.

Response filed in Egyptian Patent Application No. PCT1637/2011, dated Mar. 25, 2021, 26 pages (with English Translation).

Notice of Allowance in U.S. Appl. No. 17/067,302, dated May 28, 2021, 11 pages.

\* cited by examiner

PHARMACEUTICAL COMPOSITION FOR TREATING TUMOR

CROSS-REFERENCE TO RELATED APPLICATION

This application claims the benefit of Japanese patent application No. 2019-138041 filed on Jul. 26, 2019, the disclosure of which is herein incorporated by reference in its entirety.

TECHNICAL FIELD

The present invention relates to a pharmaceutical composition for treating tumor.

BACKGROUND

Eribulin represented by formula (I) is used as a therapeutic agent for breast cancer and soft tissue tumor.

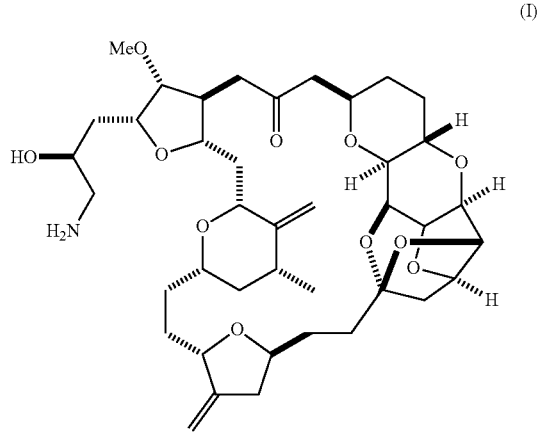

Patent Literature 1 discloses eribulin or a pharmaceutically acceptable salt thereof and a method of producing the same. Patent Literatures 2 and 3 disclose methods for producing eribulin and eribulin mesylate, which is a mesylate (methanesulfonate) thereof. Patent Literature 4 discloses a method of inhibiting growth of cancer in a patient by administering eribulin or a pharmaceutically acceptable salt thereof to the patient. Patent Literature 5 discloses a method of treating cancer in a patient by administering eribulin or a pharmaceutically acceptable salt thereof to the patient in combination with a certain second anticancer agent. Patent Literature 6 discloses a method of treating cancer in a patient by administering eribulin or a pharmaceutically acceptable salt thereof to the patient in combination with a second therapeutic approach. Patent Literatures 7 and 8 disclose liposomal compositions comprising eribulin mesylate. Patent Literature 9 discloses a method for treating breast cancer, comprising administering a combination of eribulin or a pharmaceutically acceptable salt thereof and a programmed cell death 1 protein (PD-1) antagonist.

PD-1 is recognized as an important factor in maintenance of immunoregulation and peripheral tolerance. PD-1 is moderately expressed in naive T cells, B cells, and NK T cells, and upregulated by T/B cell receptor signal transduction in lymphocytes, monocytes, and myeloid cells (Non Patent Literature 1). Meanwhile, PD-L1 is expressed in various cancer cells or T/B cells, macrophages, mDCs, plasmacytoid DCs: (pDCs), bone marrow mast cells, and the like.

The two known PD-1 ligands PD-L1 (B7-H1) and PD-L2 (B7-DC) are expressed in human cancer occurring in various tissues. For example, in a large amount of sample sets of ovarian cancer, renal cancer, colorectal cancer, pancreatic cancel; liver cancel; and melanoma, the PD-L1 expression has been shown to correlate with poor prognosis and decreased overall survival, regardless of subsequent treatment (Non Patent Literatures 2 to 13). Similarly, it was found that the PD-1 expression in tumor-infiltrating lymphocytes is characteristic of functionally impaired T cells in breast cancer and melanoma (Non Patent Literatures 14 to 15) and correlates with poor prognosis in kidney cancer (Non Patent Literature 16). Therefore, it has been proposed to block the immunosuppression mechanism that cancer cells bring, such as the interaction of tumor cells expressing PD-L1 with T cells expressing PD-1, and thereby bring the immune response to tumor.

Several monoclonal antibodies that inhibit the interaction between PD-1 and either or both of PD-1 ligands PD-L1 and PD-L2 are under clinical development for treating cancer. It has been proposed that the efficacy of such antibodies may be increased when administered in combination with another approved or experimental cancer therapy, for example, radiation, surgery, a chemotherapeutic agent, a targeted therapy, an agent that inhibits another signaling pathway that is dysregulated in tumor, and another immunostimulant.

Patent Literature 1: WO 99/65894
Patent Literature 2: WO 2005/118565
Patent Literature 3: WO 2011/094339
Patent Literature 4: U.S. Pat. No. 6,469,182
Patent Literature 5: U.S. Application Publication No. 2006/104984
Patent Literature 6: U.S. Pat. No. 6,653,341
Patent Literature 7: WO 2010/113984
Patent Literature 8: WO 2017/188350
Patent Literature 9: WO 2016/141209
Non Patent Literature 1: Sharpe, A. H, Wherry, E. J., Ahmed R, and Freeman G. J., The function of programmed cell death 1 and its ligands in regulating autoimmunity and infection. Nature Immunology (2007); 8: 239-245.
Non Patent Literature 2: Dong H et al., Tumor-associated B7-H1 promotes T-cell apoptosis: a potential mechanism of immune evasion. Nat Med. 2002 August; 8(8): 793-800.
Non Patent Literature 3: Yang et al., PD-1 interaction contributes to the functional suppression of T-cell responses to human uveal melanoma cells in vitro. Invest Ophthalmol Vis Sci. 2008 June; 49(6 (2008): 49: 2518-2525.
Non Patent Literature 4: Ghebeh et al., The B7-H1 (PD-L1) T lymphocyte-inhibitory molecule is expressed in breast cancer patients with infiltrating ductal carcinoma: correlation with important high-risk prognostic factors. Neoplasia (2006) 8: 190-198.
Non Patent Literature 5: Hamanishi J et al., Programmed cell death 1 ligand 1 and tumor-infiltrating CD8+ T lymphocytes are prognostic factors of human ovarian cancer. Proceeding of the National Academy of Sciences (2007): 104: 3360-3365.
Non Patent Literature 6: Thompson R H et al., Significance of B7-H1 overexpression in kidney cancer. Clinical genitourin Cancer (2006): 5: 206-211.
Non Patent Literature 7: Nomi, T. Sho, M., Akahori, T., et al., Clinical significance and therapeutic potential of the programmed death-1 ligand/programmed death-1 pathway in human pancreatic cancer. Clinical Cancer Research (2007); 13: 2151-2157.

Non Patent Literature 8: Ohigashi Y et al., Clinical significance of programmed death-1 ligand-1 and programmed death-1 ligand 2 expression in human esophageal cancer. Clin. Cancer Research (2005): 11: 2947-2953.

Non Patent Literature 9: Inman et al., PD-L1 (B7-H1) expression by urothelial carcinoma of the bladder and BCG-induced granulomata: associations with localized stage progression. Cancer (2007): 109: 1499-1505.

Non Patent Literature 10: Shimauchi T et al., Augmented expression of programmed death-1 in both neoplasmatic and nonneoplastic CD4+ T-cells in adult T-cell Leukemia/Lymphoma. Int. J. Cancer (2007): 121: 2585-2590.

Non Patent Literature 11: Gao et al., Overexpression of PD-L1 significantly associates with tumor aggressiveness and postoperative recurrence in human hepatocellular carcinoma. Clinical Cancer Research (2009) 15: 971-979.

Non Patent Literature 12: Nakanishi J., Overexpression of B7-H1 (PD-L1) significantly associates with tumor grade and postoperative prognosis in human urothelial cancers. Cancer Immunol Immunother. (2007) 56: 1173-1182.

Non Patent Literature 13: Hino et al., Tumor cell expression of programmed cell death-1 is a prognostic factor for malignant melanoma. Cancer (2010): 116: 1757-1766.

Non Patent Literature 14: Ghebeh H., Foxp3+ tregs and B7-H1+/PD-1+ T lymphocytes co-infiltrate the tumor tissues of high-risk breast cancer patients: implication for immunotherapy. BMC Cancer. 2008 Feb. 23; 8:57.

Non Patent Literature 15: Ahmadzadeh M. et al., Tumor antigen-specific CD8 T cells infiltrating the tumor express high levels of PD-1 and are functionally impaired. Blood (2009) 114: 1537-1544.

Non Patent Literature 16: Thompson R H et al., PD-1 is expressed by tumor infiltrating cells and is associated with poor outcome for patients with renal carcinoma. Clinical Cancer Research (2007) 15: 1757-1761.

SUMMARY

The present invention is directed to provide a new pharmaceutical composition for treating tumor.

The present inventors have studied diligently and, as a result, found that the combined administration of a liposomal composition comprising eribulin or a pharmaceutically acceptable salt thereof and a PD-1 antagonist exhibits unexpected antitumor effect, thereby completing the present invention.

Accordingly, the present disclosure is as follows.

[1] A pharmaceutical composition for treating tumor, comprising a liposomal composition comprising eribulin or a pharmaceutically acceptable salt thereof, wherein the pharmaceutical composition is administered in combination with a PD-1 antagonist.

[2] A pharmaceutical composition for treating tumor, comprising a PD-1 antagonist, wherein the pharmaceutical composition is administered in combination with a liposomal composition comprising eribulin or a pharmaceutically acceptable salt thereof.

[3] The pharmaceutical composition according to [1] or [2] above, wherein the liposomal composition comprising eribulin or a pharmaceutically acceptable salt thereof and the PD-1 antagonist are administered simultaneously, separately, continuously, or at a time interval.

[4] The pharmaceutical composition according to any of [1] to [3] above, wherein eribulin or the pharmaceutically acceptable salt thereof is eribulin mesylate.

[5] The pharmaceutical composition according to any of [1] to [4] above, wherein the PD-1 antagonist is an anti-PD-1 antibody.

[6] The pharmaceutical composition according to [5] above, wherein the anti-PD-1 antibody is selected from the group consisting of nivolumab, pembrolizumab, cemiplimab, sintilimab, and toripalimab.

[7-1] The pharmaceutical composition according to any of [1] to [6] above, wherein the tumor is selected from the group consisting of breast cancel; gastric cancer, esophageal cancer and small cell lung cancer.

[7-2] The pharmaceutical composition according to any of [1] to [6] above, wherein the tumor is breast cancer.

[8] A therapeutic agent for tumor, comprising a liposomal composition comprising eribulin or a pharmaceutically acceptable salt thereof; wherein the pharmaceutical composition is administered in combination with a PD-1 antagonist.

[9] A therapeutic agent for tumor, comprising a PD-1 antagonist, wherein the therapeutic agent is administered in combination with a liposomal composition comprising eribulin or a pharmaceutically acceptable salt thereof.

[10] The therapeutic agent according to [8] or [9] above, wherein the liposomal composition comprising eribulin or a pharmaceutically acceptable salt thereof and the PD-1 antagonist are administered simultaneously, separately, continuously, or at a time interval.

[11] The therapeutic agent according to any of [8] to [10] above, wherein eribulin or the pharmaceutically acceptable salt thereof is eribulin mesylate.

[12] The therapeutic agent according to any of [8] to [11] above, wherein the PD-1 antagonist is an anti-PD-1 antibody.

[13] The therapeutic agent according to [12] above, wherein the anti-PD-1 antibody is selected from the group consisting of nivolumab, pembrolizumab, cemiplimab, sintilimab, and toripalimab.

[14-1] The therapeutic agent according to any of [8] to [13] above, wherein the tumor is selected from the group consisting of breast cancer, gastric cancer, esophageal cancer and small cell lung cancer.

[14-2] The therapeutic agent according to any of [8] to [13] above, wherein the tumor is breast cancer.

[15] A method for treating tumor, comprising administering a liposomal composition comprising eribulin or a pharmaceutically acceptable salt thereof and a PD-1 antagonist to a patient in need thereof.

[16] The method according to [15] above, wherein the liposomal composition comprising eribulin or a pharmaceutically acceptable salt thereof and the PD-1 antagonist are administered simultaneously, separately, continuously, or at a time interval.

[17] The method according to [15] or [16] above, wherein eribulin or the pharmaceutically acceptable salt thereof is eribulin mesylate.

[18] The method according to any of [15] to [17] above, wherein the PD-1 antagonist is an anti-PD-1 antibody.

[19] The method according to [18] above, wherein the anti-PD-1 antibody is selected from the group consisting of nivolumab, pembrolizumab, cemiplimab, sintilimab, and toripalimab.

[20-1] The method according to any of [15] to [19] above, wherein the tumor is selected from the group consisting of breast cancer, gastric cancer, esophageal cancer and small cell lung cancer.

[20-2] The method according to any of [15] to [19] above, wherein the tumor is breast cancer.

[21] Use of eribulin or a pharmaceutically acceptable salt thereof in the manufacture of a pharmaceutical composition for treating tumor, wherein the pharmaceutical composition is administered in combination with a PD-1 antagonist.

[22] Use of a PD-1 antagonist in the manufacture of a pharmaceutical composition for treating tumor, wherein the pharmaceutical composition is administered in combination with a liposomal composition comprising eribulin or a pharmaceutically acceptable salt thereof.

[23] The use according to [21] or [22] above, wherein the liposomal composition comprising eribulin or a pharmaceutically acceptable salt thereof and the PD-1 antagonist are administered simultaneously, separately, continuously, or at a time interval.

[24] The use according to any of [21] to [23] above, wherein eribulin or the pharmaceutically acceptable salt thereof is eribulin mesylate.

[25] The use according to any of [21] to [24] above, wherein the PD-1 antagonist is an anti-PD-1 antibody.

[26] The use according to [25] above, wherein the anti-PD-1 antibody is selected from the group consisting of nivolumab, pembrolizumab, cemiplimab, sintilimab, and toripalimab.

[27-1] The use according to any of [21] to [26] above, wherein the tumor is selected from the group consisting of breast cancer, gastric cancer, esophageal cancer and small cell lung cancer.

[27-2] The use according to any of [21] to [26] above, wherein the tumor is breast cancer.

[28] A liposomal composition comprising eribulin or a pharmaceutically acceptable salt thereof for use in tumor treatment, wherein the liposomal composition is administered in combination with a PD-1 antagonist.

[29] A PD-1 antagonist for use in tumor treatment, wherein the PD-1 antagonist is administered in combination with a liposomal composition comprising eribulin or a pharmaceutically acceptable salt thereof.

[30] The liposomal composition or PD-1 antagonist for use according to [28] or [29] above, wherein the liposomal composition comprising eribulin or a pharmaceutically acceptable salt thereof and the PD-1 antagonist are administered simultaneously, separately, continuously, or at a time interval.

[31] The liposomal composition or PD-1 antagonist for use according to any of [28] to [30] above, wherein eribulin or the pharmaceutically acceptable salt thereof is eribulin mesylate.

[32] The liposomal composition or PD-1 antagonist for use according to any of [28] to [31] above, wherein the PD-1 antagonist is an anti-PD-1 antibody.

[33] The liposomal composition or PD-1 antagonist for use according to [32] above, wherein the anti-PD-1 antibody is selected from the group consisting of nivolumab, pembrolizumab, cemiplimab, sintilimab, and toripalimab.

[34-1] The liposomal composition or PD-1 antagonist for use according to [28] to [33] above, wherein the tumor is selected from the group consisting of breast cancer, gastric cancer, esophageal cancer and small cell lung cancer.

[34-2] The liposomal composition or PD-1 antagonist for use according to [28] to [33] above, wherein the tumor is breast cancer.

[35] A kit for treating tumor, comprising a formulation comprising a liposomal composition comprising eribulin or a pharmaceutically acceptable salt thereof and a formulation comprising a PD-1 antagonist.

[36] The kit according to [35] above, wherein the liposomal composition comprising eribulin or a pharmaceutically acceptable salt thereof and the PD-1 antagonist are administered simultaneously, separately, continuously, or at a time interval.

[37] The kit according to [35] or [36] above, wherein eribulin or the pharmaceutically acceptable salt thereof is eribulin mesylate.

[38] The kit according to any of [35] to [37] above, wherein the PD-1 antagonist is an anti-PD-1 antibody.

[39] The kit according to [38] above, wherein the anti-PD-1 antibody is selected from the group consisting of nivolumab, pembrolizumab, cemiplimab, sintilimab, and toripalimab.

[40-1] The kit according to any of [35] to [39] above, wherein the tumor is selected from the group consisting of breast cancer, gastric cancel; esophageal cancer and small cell lung cancer.

[40-2] The kit according to any of [35] to [39] above, wherein the tumor is breast cancer

[41] The pharmaceutical composition according to any of [1] to [7-2] above or therapeutic agent according to any of [8] to [14-2] above, further comprising a pharmaceutically acceptable carrier.

The combined administration of a liposomal composition comprising eribulin or a pharmaceutically acceptable salt thereof and a PD-1 antagonist exhibits unexpected antitumor effect.

DETAILED DESCRIPTION

Figure 1:
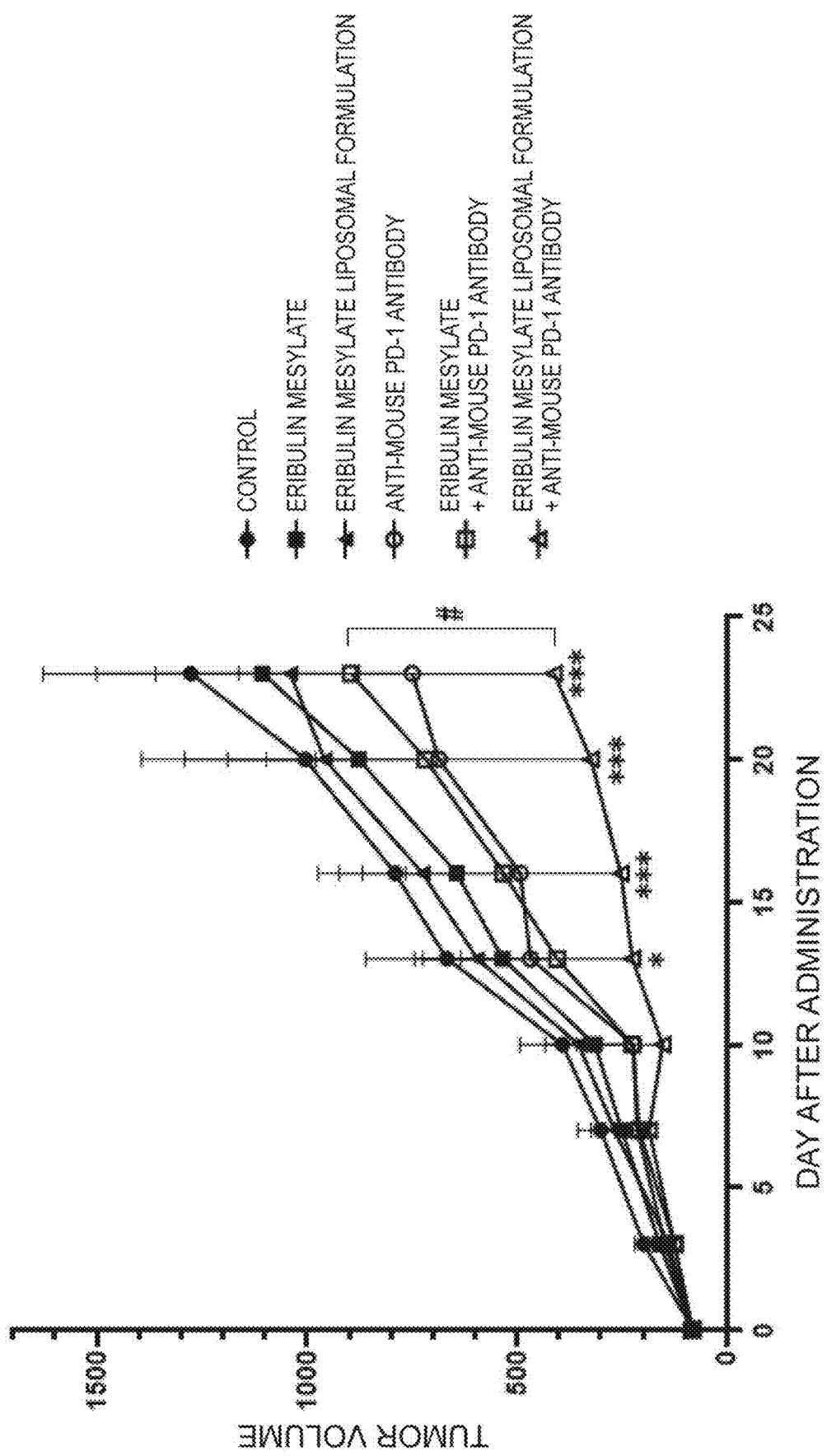
FIG. 1 is a graph illustrating effect of treatment with a combination of a liposomal formulation comprising eribulin mesylate at a dose of 0.1 mg/kg and an anti-PD-1 antibody on tumor growth.

Embodiments of the present disclosure will be described below. The following embodiments are illustrations for the purpose of describing the present disclosure and not intended to limit the present disclosure only to these embodiments. The present disclosure can be carried out in various forms, unless they deviate from its spirit.

The liposomal compositions in the present disclosure comprises eribulin or a pharmaceutically acceptable salt thereof (hereinafter referred to as "eribulin or the like").

In the present disclosure, the "pharmaceutically acceptable salt" may be either an inorganic acid salt or an organic acid salt and is not particularly limited, as long as it forms a salt with eribulin, and examples thereof include hydrochloride, sulfate, citrate, hydrobromide, hydroiodide, nitrate, bisulfate, phosphate, superphosphate, isonicotinate, acetate, lactate, salicylate, tartrate, pantothenate, ascorbate, succinate, maleate, fumarate, gluconate, saccharinate, formate, benzoate, glutamate, mesylate (methanesulfonate), ethanesulfonate, benzenesulfonate, p-toluenesulfonate, and pamoate. In one embodiment, the pharmaceutically acceptable salts are hydrochloride, sulfate, acetate, phosphate, citrate, and mesylate. In a particular embodiment, the pharmaceutically acceptable salt is mesylate.

The pharmaceutically acceptable salt of eribulin may be a salt of eribulin and aluminum, calcium, lithium, magnesium, sodium, zinc, or diethanolamine.

In the present disclosure, examples of eribulin or the like include eribulin mesylate.

Eribulin or the like is a compound or a salt thereof described in Patent Literature 1 or U.S. Pat. No. 6,214,865 and has pharmacological activities including antitumor and antimitotic activities. Patent Literature 1 discloses that eribulin or the like has, as an antitumor agent, anti-tumor activity against melanoma, fibrosarcoma, monocytic leukemia, colon cancer, ovarian cancer, breast cancer, osteosarcoma, prostate cancer, lung cancer, and ras-transformed fibroblasts. Eribulin or the like is obtained by a method of production described in Patent Literatures 1 to 3.

In the present disclosure, the "liposome" means a closed microvesicle having an inner phase surrounded by a lipid bilayer. The liposomes include small unilamellar liposomes (SUVs: small unilamellar vesicles), large unilamellar liposomes (LUVs: large unilamellar vesicles), further large unilamellar liposomes (GUVs: giant unilamellar vesicles), multi-lamellar liposomes having a plurality of concentric membranes (MVs: multi lamellar vesicles), liposomes having a plurality of non-concentric, irregular membranes (MVVs: multivesicular vesicles), and the like.

In the present disclosure, the "liposomal inner phase" means an aqueous region surrounded by a liposomal lipid bilayer and is used synonymously with an "inner aqueous phase" and a "liposomal inner aqueous phase". The "liposomal outer phase" means a region that is not surrounded by a liposomal lipid bilayer (that is, the region except the inner phase and the lipid bilayer) when the liposome is dispersed in a liquid.

In the present disclosure, the "liposomal composition" means a composition comprising a liposome and further comprising eribulin or the like in the liposomal inner phase. In the present disclosure, the liposomal composition includes solid and liquid compositions.

In the present disclosure, the "liposomal dispersion liquid" means a composition comprising a liposome in which eribulin or the like is not yet encapsulated into the liposomal inner phase.

In the present disclosure, the "liposomal preparatory liquid" means a composition comprising a liposome in which an adjustment of the liposome outer phase in order to encapsulate eribulin or the like into the liposome inner phase is not yet performed.

[Lipid]

In one embodiment, the liposome preferably comprises a phospholipid and/or a phospholipid derivative as a membrane component.

Examples of the phospholipid and/or phospholipid derivative include phosphatidylethanolamine, phosphatidylcholine, phosphatidylserine, phosphatidylinositol, phosphatidylglycerol, cardiolipin, sphingomyelin, ceramide phosphoryl ethanolamine, ceramidephosphorylglycerol, ceramidephosphorylglycerolphosphate, 1,2-dimyristoyl-1,2-deoxyphosphatidyl choline, plasmalogen, and phosphatidate.

The phospholipid and/or phospholipid derivative may be one or a combination of two or more of these.

Fatty acid residues in the phospholipid and/or phospholipid derivative are not particularly limited, and examples thereof include saturated or unsaturated fatty acid residues having 12 to 20 carbon atoms, and specific examples thereof include acyl groups derived from fatty acids such as lauric acid, myristic acid, palmitic acid, stearic acid, oleic acid, and linoleic acid. As the phospholipid and/or phospholipid derivative, a phospholipid derived from a natural product such as egg yolk lecithin and soy lecithin, and partially hydrogenated egg yolk lecithin, (fully) hydrogenated egg yolk lecithin, partially hydrogenated soy lecithin, and (fully) hydrogenated soybean lecithin, in which unsaturated fatty acid residues are partially or fully hydrogenated, or the like may be used.

The amount (molar fraction) of the phospholipid and/or phospholipid derivative, used in the preparation of the liposome, that are/is blended is not particularly limited, and is, in one embodiment, 10 to 80% and, in a particular embodiment, 30 to 60% based on the total ribosomal membrane components.

In the present disclosure, the liposome may comprise, as a membrane component, a sterol such as cholesterol and cholestanol and a fatty acid having a saturated or unsaturated acyl group having 8 to 22 carbon atoms as a membrane stabilizing agent, and an antioxidant such as α-tocopherol, besides the phospholipid and/or phospholipid derivative.

The amount (molar fraction) of the sterol, used in the preparation of the liposome, that is blended is not particularly limited, and is, in one embodiment, 1 to 60%, 10 to 50%, or 30 to 50% based on the total liposomal membrane components.

The amount (molar fraction) of the fatty acid blended is not particularly limited, and is, in one embodiment, 0 to 30% and 0 to 20% or 0 to 10% based on the total liposomal membrane components.

The amount (molar fraction) of the antioxidant blended is not particularly limited, as long as an amount that provides the antioxidant effect is added, and it is, in one embodiment, 0 to 15%, 0 to 10%, or 0 to 5% based on the total liposomal membrane components.

In the present disclosure, the liposome may comprise a functional lipid or a modified lipid as a membrane component.

Examples of the functional lipid include a blood-retaining lipid derivative, a temperature change-sensitive lipid derivative, and a pH-sensitive lipid derivative.

Examples of the modified lipid include a PEGylated lipid, a glycolipid, an antibody-modified lipid, and a peptide-modified lipid.

Examples of the blood-retaining lipid derivative include polyethylene glycol derivatives (such as methoxy polyethylene glycol condensates) such as condensation products of phosphoethanolamine and methoxy polyethylene glycol: N-{carbonyl-methoxy polyethylene glycol-2000}-1,2-dipalmitoyl-sn-glycero-3-phosphoethanolamine, N-{carbonyl-methoxy polyethylene glycol-5000}-1,2-dipalmitoyl-sn-glycero-3-phosphoethanolamine, N-{carbonyl-methoxy polyethylene glycol-750}-1,2-distearoyl-sn-glycero-3-phosphoethanolamine, N-{carbonyl-methoxy polyethylene glycol-2000}-1,2-distearoyl-sn-glycero-3-phosphoethanolamine, (MPEG2000-distearoylphosphatidylethanolamine), and N-{carbonyl-methoxy polyethylene glycol-5000}-1,2-distearoyl-sn-glycero-3-phosphoethanolamine.

The blending amount (molar fraction) of the blood-retaining lipid derivative, used in the preparation of the liposome, is not particularly limited, and is, in one embodiment, 0 to 50%, 0 to 30%, or 0 to 20% based on the total liposomal membrane components.

Examples of the temperature change-sensitive lipid derivative include dipalmitoylphosphatidylcholine. By including a temperature change-sensitive lipid derivative in a liposome, it becomes possible to disrupt the liposome at a particular temperature, to change the surface properties of the liposome, and the like. Furthermore, by combining it with heating of a target site such as tumor, it becomes possible to disrupt the liposome at the target site and have an active compound released at the target site, and the like.

Examples of the pH-sensitive lipid derivative include dioleoylphosphatidylethanolamine. By including a pH-sensitive lipid derivative in a liposome, it becomes possible to promote membrane fusion of the liposome and an endosome when the liposome is taken in a cell by endocytosis and improve the delivery of the active compound to the cytoplasm, and the like.

Examples of the glycolipid, antibody-modified lipid, and peptide-modified lipid include lipids linked to a sugar, an antibody, or a peptide having an affinity for a target cell or a target tissue. Using a modified lipid allows to deliver the liposome actively to the target cell or the target tissue.

The composition of membrane components for liposome having a practically acceptable level of membrane permeability can be set by a person skilled in the art as appropriate depending on the active compound, the target tissue, and the like (see Hiroshi Kikuchi et al. "Liposome I-How to prepare and assay-(in Japanese)" Cell technology (1983) 2 (9): pp. 1136-1149 and the references cited in the reference, and the like). The liposomal composition may be used not only in targeting at a target tissue such as solid cancer, but also in the delivery of an active compound to blood cancer or the like.

The liposomal membrane components include, in one embodiment, phospholipid, cholesterol, and a methoxy polyethylene glycol condensation product.

[Liposomal Composition]

In the liposomal composition in the present disclosure, eribulin or the like is encapsulated in a liposome having a lipid membrane. In the liposomal composition, eribulin or the like may be distributed in the lipid bilayer.

The liposomal composition according to the present disclosure can be obtained by a method described in Patent Literature 7.

If the liposomal composition is solid, the solid liposomal composition may be dissolved or suspended in a certain solvent described below to prepare a liquid liposomal composition. In case that the liposomal composition is a frozen solid, the frozen solid liposomal composition may be thawed by leaving the composition at room temperature or the like to prepare a liquid liposomal composition.

The liposomal composition according to the present disclosure is not limited, as long as it comprises (1) eribulin or the like. The liposomal composition according to the present disclosure may further comprise (2) at least one ammonium salt and (3) at least one acid, salt, base, and/or amino acid.

Examples of the at least one ammonium salt (2) include ammonium chloride, ammonium borate, ammonium sulfate, ammonium formate, ammonium acetate, ammonium ciliate, ammonium tartrate, ammonium succinate, and ammonium phosphate and, in one embodiment, the at least one ammonium salt (2) is ammonium sulfate, ammonium citrate, and ammonium tartrate.

As for the acid, salt, base, and/or amino acid (3), examples of the acid include ascorbic acid, benzoic acid, succinic acid, citric acid, glutamic acid, phosphoric acid, acetic acid, propionic acid, tartaric acid, carbonic acid, lactic acid, boric acid, maleic acid, fumaric acid, malic acid, adipic acid, hydrochloric acid, and sulfuric acid; examples of the salt include sodium salts of the aforementioned acids, potassium salts of the aforementioned acids, and ammonium salts of the aforementioned acids; examples of the base include trishydroxymethylaminomethane, ammonia, sodium hydroxide, and potassium hydroxide; and examples of the amino acid include arginine, histidine, and glycine.

In one embodiment of the liposomal composition according to the present disclosure, the acid, salt, base, and/or amino acid (3) in the liposomal inner phase is hydrochloric acid, acetic acid, lactic acid, tartaric acid, succinic acid, citric acid, and phosphoric acid, sodium salts of the aforementioned acids, and sodium hydroxide and ammonia, and, in a particular embodiment, the acid, salt, base, and/or amino acid (3) is acetic acid, lactic acid, tartaric acid, citric acid, and phosphoric acid, sodium salts of the aforementioned acids, and sodium hydroxide and ammonia.

An example of the components of the liposomal composition is set forth in Table 1. In another specific example, 96 mg/mL sucrose may be used, instead of 9 mg/mL sodium chloride, as an osmotic agent (liposomal outer phase).

TABLE 1

| Component | Concentration | Purpose of inclusion |
| --- | --- | --- |
| Eribulin mesylate | 0.2 mg/mL | Drug |
| HSPC[1] | 7.1 mg/mL | Lipid membrane component |
| Cholesterol | 2.3 mg/mL | Lipid membrane component |
| MPEG2000-DSPE[2] | 2.7 mg/mL | Lipid membrane component |
| Ammonium sulfate | 100 mM | Liposomal inner phase component |
| Citric acid monohydrate | 30 mM | Liposomal inner phase component |
| Sodium chloride | 9 mg/mL | Liposomal outer phase component |
| L-histidine | 1.6 mg/mL | Liposomal outer phase component |
| Sodium hydroxide/ hydrochloric acid | q.s. | pH adjuster |

[1]Hydrogenated soy phosphatidylcholine
[2]N-{carbonyl-methoxy polyethylene glycol-2000}-1,2-distearoyl-sn-glycero-3-phosphoethanolamine (MPEG2000-distearoylphosphatidylethanolamine)

The liposomal composition according to the present disclosure may be administered by injection (intravenous injection, intraarterial injection, local injection), orally, nasally, transdermally, transpulmonarily, ophthalmically, and the like, and examples thereof include injection such as intravenous injection, subcutaneous injection, intradermal injection, intraarterial injection, as well as local injection to a target cell and organ. Examples of the dosage form of the liposomal composition for oral administration include tablets, powders, granules, syrups, capsules, and oral solutions. Examples of the dosage form of the liposomal composition for parenteral administration include injections, drip infusions, ophthalmic liquids, ointments, suppositories, suspensions, cataplasms, lotions, aerosols, and plasters, and, in one embodiment, the liposomal composition for parenteral administration is an injection or a drip infusion. The liposomal composition according to the present disclosure may be formulated by a method, for example, described in Japanese Pharmacopoeia (JP) 17th edition, United States Pharmacopoeia (USP), or European pharmacopoeia (EP).

In a case that the liposomal composition is a liquid, the liposomal composition may be used as it is. To use the liposomal composition as a medicine, for example, a solvent may be injected by a physician or a patient into a vial in which a solid formulation is encapsulated to do such preparation upon use. A solid formulation obtained by freezing a liquid liposomal composition may be stored in a frozen state and thawed by leaving at room temperature or thawed rapidly with heating back into a liquid upon use to be used as a liquid.

The dose upon administration of the liposomal composition alone vary markedly depending on the kind of the target disease, the age, sex, body weight of the patient, the severity of symptoms, and the like. The liposomal composition is administered, for example, at 0.1 to 10 mg/m$^2$ (body surface) in terms of eribulin mesylate per day for an adult. In one embodiment, the liposomal composition is administered at a dose of 0.5 to 3 mg/m$^2$ (body surface) in terms of eribulin mesylate once every 1 week, 2 weeks, or 3 weeks. In a particular embodiment, the liposomal composition is more preferably administered at a dose of 0.5 to 2 mg/m$^2$ (body surface) in terms of eribulin mesylate once every 1 week, 2 weeks, or 3 weeks.

In another aspect, the liposomal composition is preferably administered at a dose of approximately 1.5 mg/m$^2$ (body surface) in terms of eribulin mesylate once every 1 week, 2 weeks, or 3 weeks.

More specifically, the liposomal composition is administered intravenously at 0.5 to 1.4 mg/m$^2$ on day 1 of a 21-day cycle or administered intravenously at 0.5 to 1.5 mg/m$^2$ on day 1 and day 15 of a 28-day cycle in terms of eribulin mesylate.

Eribulin or the like contained in the liposomal composition may be administered once a day or in several divided daily doses.

The liposomal composition may be a liposomal composition comprising, for example, 0.01 to 300 mg/mL of eribulin or the like in the liposomal inner phase.

The liposomal composition is formulated, for example, as an injection comprising 0.20 mg/mL eribulin mesylate (0.18 mg/mL eribulin) incorporated in a liposome having a lipid membrane consisting of HSPC, cholesterol, and MPEG2000-DSPE. Such an injection may comprise sucrose or sodium chloride as an isotonizing agent, ammonium sulfate, citric acid, and L-histidine, and sodium hydroxide and hydrochloric acid to adjust pH. The injection is directly administered to a patient or diluted with physiological saline to a concentration in the range of 0.0035 mg/mL or higher and lower than 0.2 mg/mL before the administration to a patient.

The PD-1 antagonist in the present disclosure may comprise any compound or biological molecule that blocks the binding of PD-L1 expressed in cancer cells to PD-1 expressed in immune cells (T cells, B cells, or natural killer T (NKT) cells), or that blocks the binding of PD-L2 expressed in cancer cells to PD-1 expressed in immune cells. The PD-1 antagonist blocks the binding of human PD-L1 to human PD-1 and, in one embodiment, blocks the binding of both human PD-L1 and PD-L2 to human PD-1. The amino acid sequence of human PD-1 can be found in NCBI Locus No.: NP_005009. The amino acid sequences of human PD-L1 and PD-L2 can be found in NCBI Locus No: NP 054862 and NP_079515, respectively.

The PD-1 antagonist useful in the present disclosure may comprise a monoclonal antibody (mAb) or an antigen-binding fragment thereof that specifically binds to PD-1 or PD-L1 or that specifically binds to human PD-1 or human PD-L1. The mAb may be a human antibody, a humanized antibody, or a chimeric antibody and may comprise a human constant region. The human constant region is selected from the group consisting of IgG1, IgG2, IgG3, and IgG4 constant regions and, in one embodiment, the human constant region is an IgG1 or IgG4 constant region. The antigen-binding fragment may be selected from the group consisting of Fab, Fab'-SH, F(ab')$_2$, scFv, and Fv fragment.

An example of useful PD-1 antagonists is an anti-PD-1 antibody, which is, in one embodiment, an anti-human PD-1 antibody and, in a particular embodiment, an anti-human PD-1 monoclonal antibody (anti-human PD-1 mAb). Examples of the human PD-1-binding mAb binding are described in U.S. Pat. Nos. 7,488,802, 7,521,051, 8,008,449, 8,354,509, 8,168,757, WO 2004/004771, WO 2004/072286, WO 2004/056875, and US Patent Application Publication No. 2011/0271358. Anti-human PD-1 monoclonal antibodies useful as the PD-1 antagonist according to the present disclosure include nivolumab, pembrolizumab, cemiplimab, sintilimab, and toripalimab.

The PD-1 antagonist according to the present disclosure may be administered by injection (intravenous injection, intraarterial injection, local injection), orally, nasally, transdermally, transpulmonarily, ophthahmically, and the like and examples thereof include injection such as intravenous injection, subcutaneous injection, intradermal injection, intraarterial injection, as well as local injection to target cells and organ. Examples of the dosage form of the PD-1 antagonist for oral administration include tablets, powders, granules, syrups, capsules, and oral solutions. Examples of the dosage form of the PD-1 antagonist for parenteral administration include injections, drip infusions, ophthalmic liquids, ointments, suppositories, suspensions, cataplasms, lotions, aerosols, and plasters and in one embodiment, the dosage form of the PD-1 antagonist for parenteral administration is an injection or a drip infusion. The PD-1 antagonist according to the present disclosure may be formulated by a method, for example, described in Japanese Pharmacopoeia (JP) 17th edition, United States Pharmacopoeia (USP), or European pharmacopoeia (EP).

If the PD-1 antagonist according to the present disclosure is an anti-PD-1 antibody, the anti-PD-1 antibody may be provided as a liquid preparation or prepared by rehydrating freeze-drying powder with sterile water for injection before use.

Upon administration of an anti-human PD-1 mAb alone as the PD-1 antagonist to a patient, the dose thereof varies markedly depending on the kind of the target disease, the age, sex, body weight of the patient, the severity of symptoms, and the like. The anti-human PD-1 mAb is administered, for example, at a dose of 1, 2, 3, 5, or 10 mg/kg at intervals of approximately 14 days (±2 days), approximately 21 days (±2 days), or approximately 30 days (±2 days).

When pembrolizumab is administered as the PD-1 antagonist, pembrolizumab is, for example, administered intravenously at a dose selected from the group consisting of 1 mg/kg Q2W, 2 mg/kg Q2W, 3 mg/kg Q2W, 5 mg/kg Q2W, 10 mg of Q2W, 1 mg/kg Q3W, 2 mg/kg Q3W, 3 mg/kg Q3W, 5 mg/kg Q3W, and 10 mg Q3W. Pembrolizumab is administered as a liquid medicine, for example, comprising 25 mg/ml pembrolizumab, 7% (w/v) sucrose, and 0.02% (w/v) polysorbate 80 in a 10 mM histidine buffer, pH 5.5, and a selected dose of the medicine is administered by IV injection over a period of approximately 30 minutes.

When nivolumab is administered as the PD-1 antagonist, nivolumab is, for example, administered intravenously at a dose selected from the group consisting of 1 mg/kg Q2W, 2 mg/kg Q2W, and 3 mg/kg Q2W.

The doses of the liposomal composition and the PD-1 antagonist in the combined administration of the present disclosure may usually be set at doses lower than the doses when they are administered alone. Specific doses, administration routes, administration frequencies, and administration cycles are determined as appropriate in consideration of the kind of the target disease, the age, sex, body weight of the patient, the severity of symptoms, and the like.

The mode of administration of the liposomal composition and the PD-1 antagonist in the present disclosure is not particularly limited, as long as the liposomal composition and the PD-1 antagonist are administered in combination when they are administered. For example, the liposomal composition and the PD-1 antagonist are administered to a patient simultaneously, separately, continuously, or at a time interval. Here, "simultaneously" means that each component is administered in the same period of time or strictly simultaneously or via the same administration route. "Separately" means that each component is administered at different dose intervals or frequencies or via different administration routes.

"Continuously" means that each component is administered via the same administration route or different administration routes in any order within a certain period of time. "At a time interval" means that each component is administered via the same administration route or different administration routes, with each component administered at a time interval. When the PD-1 antagonist is administered in a period of 1 cycle of the administration of the liposomal composition or in a period in which the cycle is repeated, it is considered that both are administered in combination.

Tumors to be treated in the present disclosure are, for example, breast cancer, gastric cancer, esophageal cancer, small cell lung cancer, colorectal cancer, and kidney cancer.

EXAMPLES

Example 1

Antitumor Effect of Combined Administration of Low Dose of Eribulin Mesylate (0.1 mg/kg) or Low Dose of Eribulin Mesylate Liposomal Formulation (0.1 mg/kg) and Anti-Mouse PD-1 Antibody in Syngeneic Transplantation Model of Murine Breast Cancer 4T1 Cell Line (Pgp-KO 4T1) with P Glycoprotein Knock-Out A P glycoprotein-knockout cell line produced from murine breast cancer 4T1 cells (purchased from ATCC) was cultured using RPMI1640 medium (SIGMA) containing 10% of FBS (fetal bovine serum), 1 mM sodium pyruvate, and antibiotics, under conditions at 37° C. in a 5% carbon dioxide gas incubator. The cells were collected using trypsin-EDTA when the cells reached to approximately 80% confluency. The medium described above (RPMI1640) was added to the collected cells, a suspension was prepared at $1.0 \times 10^7$ cells/mL, and 0.1 mL of the suspension was subcutaneously transplanted at the right body side into 6 mice (BALB/cAJcl, CLEA Japan, Inc.) per each group of the control group, eribulin mesylate alone administration group, eribulin mesylate liposomal formulation alone administration group, the anti-mouse PD-1 antibody (Bio X cell) alone administration group, eribulin mesylate and anti-mouse PD-1 antibody combined administration group, and eribulin mesylate liposomal formulation and anti-mouse PD-1 antibody combined administration group. From day 5 post-transplantation, eribulin mesylate (0.1 mg/kg, once a week, twice in total, tail vein injection), eribulin mesylate liposomal formulation (0.1 mg/kg, once a week, twice in total, tail vein injection), and the anti-mouse PD-1 antibody (200 μg/mouse, once a week, twice in total, tail vein injection) were each administered alone or in combination to the alone administration groups or the anti-mouse PD-1 antibody combined administration groups. No drug was administered to the control group. The maximum tolerated dose of eribulin mesylate liposomal formulation in mice is 2.5 mg/kg and the dose in this experiment was set very low at 0.1 mg/kg, which is 1/25 of the maximum tolerated dose.

The liposomal composition comprising eribulin mesylate was prepared with the components set forth in Table 1 in accordance with the following method.

<Preparation of Aqueous Solution for Liposomal Inner Phase>

Ammonium sulfate and citric acid monohydrate were dissolved and diluted with pure water to prepare an aqueous solution of 200 mM ammonium sulfate/60 mM citric acid. The aqueous solution of 200 mM ammonium sulfate/60 mM citric acid was adjusted to pH 5.5 with an aqueous ammonium solution and then diluted with pure water to obtain an aqueous solution of 100 mM ammonium sulfate/30 mM citric acid.

<Preparation of Liposomal Preparatory Liquid>

Hydrogenated soy phosphatidylcholine, cholesterol, and MPEG2000-distearoylphosphatidylethanolamine were weighted in accordance with a weight ratio of 71:23:27, respectively. These were each dissolved in chloroform and these solutions were mixed. Chloroform was then evaporated under reduced pressure in a rotary evaporator to prepare a lipid film. To the obtained lipid film, the prepared aqueous solution for liposomal inner phase heated to approximately 80° C. was added and the resulting mixture was stirred to prepare a liposomal preparatory liquid. Sizing was performed using an extruder (a product made by Lipex Biomembranes Inc.) heated to approximately 80° C. to obtain a sized liposomal preparatory liquid.

<Preparation of Liposomal Dispersion Liquid>

By eluting the obtained liposomal preparatory liquid through a Sephadex G-50 column with an aqueous solution of 0.9% sodium chloride/10 mM histidine (pH=7.6), the liposomal outer phase was exchanged into an aqueous solution of 0.9% sodium chloride/10 mM histidine. After exchanging the liposomal outer phase, the liquid was centrifuged at 400,000×g for 30 minutes. After the centrifugation, re-dispersion was performed and the liquid volume was adjusted with an aqueous solution of 0.9% sodium chloride/ 10 mM histidine to obtain a liposomal dispersion liquid.

<Preparation of Eribulin Mesylate Solution>

0.9% of eribulin mesylate was dissolved in an aqueous solution of sodium chloride/10 mM histidine to obtain an eribulin mesylate solution.

<Preparation of Liposomal Composition>

The liposomal dispersion liquid and eribulin mesylate solution were mixed in a glass container and incubated in a water bath at 60° C. for 3 minutes to obtain a liposomal composition with a liposomal inner phase in which eribulin mesylate was introduced. An aqueous solution of 0.9% sodium chloride/10 mM histidine was added to the liposomal composition and filter sterilization was performed with a 0.22 μm polyvinylidene fluoride (PVDF) filter to obtain an eribulin mesylate liposomal composition.

On day 3, day 7, day 10, day 13, day 16, day 20, day 23, day 27, day 30, and day 34 after administration, with the starting date of administration being day 0, the longest diameter and the short axis of the tumor grown in each mouse were measured with a digimatic caliper (a product made by Mitutoyo Corporation).

The tumor volume was calculated in accordance with the following formula.

Tumor volume (mm$^3$)=longest diameter (mm)×short axis (mm$^2$)/2

The results of measurement of the tumor volume in each group are illustrated as mean and standard deviation (SD) in FIG. 1. As statistical analysis, repeated measures analysis of variance (ANOVA) followed by Dunnett's multiple comparison was conducted in comparison with the control group for tumor volumes on all measurement days in all groups (*: p<0.05, ***: p<0.001). The statistical comparison between the two groups of eribulin mesylate and anti-mouse PD-1 antibody combined administration group and eribulin mesylate liposomal formulation and anti-mouse PD-1 antibody combined administration group was conducted by repeated measures ANOVA (#:p<0.05).

As a result, the combined administration of a low dose of eribulin mesylate liposomal formulation (0.1 mg/kg) and an anti-mouse PD-1 antibody exhibited a remarkable antitumor effect in comparison with the control group in the Pgp-KO 4T1 syngeneic tumor transplantation model. * and *** in FIG. 1 indicate that the combined administration of eribulin mesylate liposomal formulation and the anti-mouse PD-1 antibody statistically significantly inhibited tumor growth in comparison with the control group. # indicates that the combined administration of eribulin mesylate liposomal formulation and the anti-mouse PD-1 antibody statistically significantly inhibited tumor growth in comparison with the combined administration of eribulin mesylate and the anti-mouse PD-1 antibody. In contrast, no antitumor effect was observed at low doses with eribulin mesylate (0.1 mg/kg) alone administration, eribulin mesylate liposomal formulation (0.1 mg/kg) alone administration, the anti-mouse PD-1 antibody alone administration, and even the combined administration of eribulin mesylate (0.1 mg/kg) and the anti-mouse PD-1 antibody.

Figure 2:
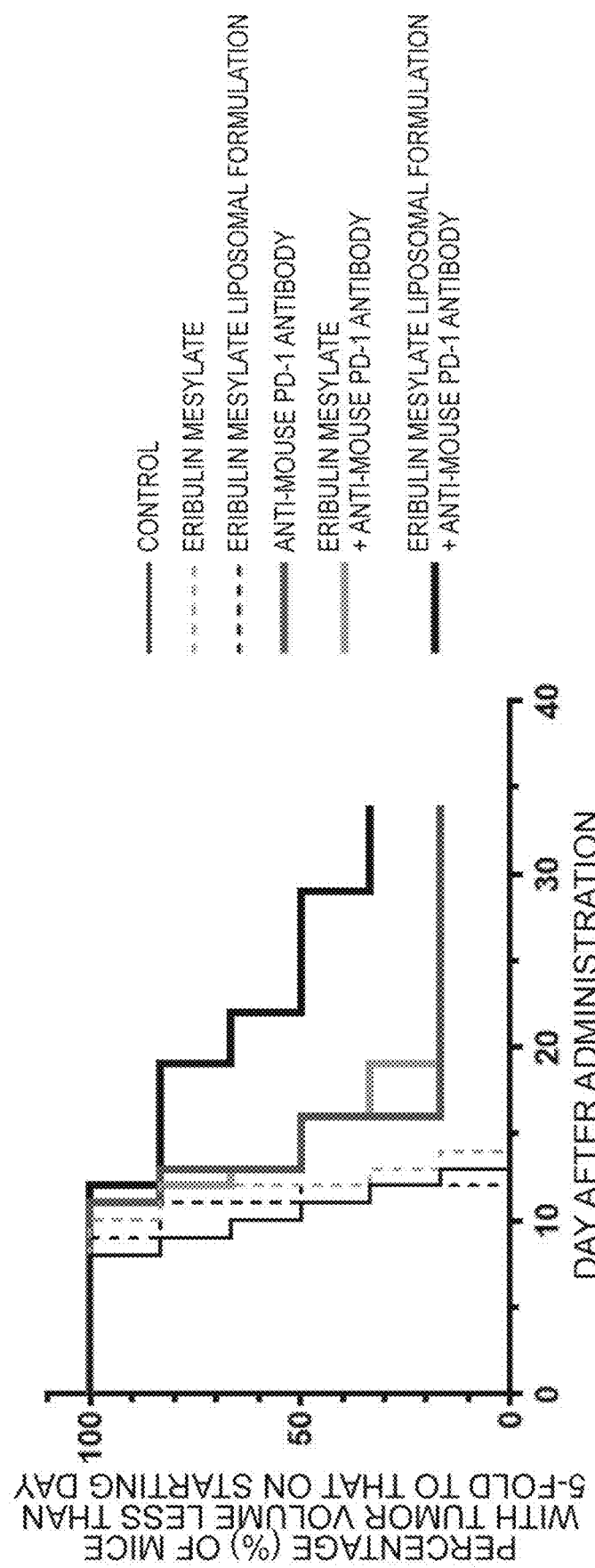
FIG. 2 is a graph illustrating effect of treatment with a combination of a liposomal formulation comprising eribulin mesylate at a dose of 0.1 mg/kg and an anti-PD-1 antibody on T×5.

The result of comparison of the groups for the time until the tumor volume exceeds 5 times that on the starting date of administration (T×5) in the experiment is shown in FIG. 2 and the median of T×5 in each group and the percentage (%) thereof to the control group are set forth in Table 2. For statistical analysis, a log-rank test was conducted in comparison with the control group to calculate the Bonferroni-corrected p-value (*: p<0.05).

As a result, the combined administration of eribulin mesylate liposomal formulation (0.1 mg/kg) and the anti-mouse PD-1 antibody exhibited the effect of extending (243%) the time of suppressing tumor growth (T×5) in Pgp-KO 4T1 syngeneic tumor transplantation model. In contrast, no extension effect was observed at low doses with eribulin mesylate (0.1 mg/kg) alone administration, eribulin mesylate liposomal formulation (0.1 mg/kg) alone administration, the anti-mouse PD-1 antibody alone administration, and further the combined administration of eribulin mesylate and the anti-mouse PD-1 antibody. * in Table 2 indicates that the combined administration of eribulin mesylate liposomal formulation (0.1 mg/kg) and the anti-mouse PD-1 antibody statistically significantly extended the time of tumor growth suppression in comparison with the control group.

TABLE 2

Effect of the combined administration of eribulin mesylate liposomal formulation (0.1 mg/kg) and anti-mouse PD-1 antibody on T × 5

| Group | T × 5 (days) | Percentage to control |
|---|---|---|
| Control | 10.5 | 100% |
| Eribulin mesylate Alone | 12.0 | 114% |
| Eribulin mesylate liposomal formulation Alone | 11.5 | 110% |
| Anti-mouse PD-1 antibody Alone | 14.5 | 138% |
| Eribulin mesylate + Anti-mouse PD-1 antibody Combined administration | 14.5 | 138% |
| Eribulin mesylate liposomal formulation + Anti-mouse PD-1 antibody Combined administration | 25.5* | 243% |

Example 2

Antitumor Effect of Combined Administration of Low Dose of Eribulin Mesylate (0.3 mg/kg) or Low Dose of Eribulin Mesylate Liposomal Formulation (0.3 mg/kg) and Anti-Mouse PD-1 Antibody in Pgp-KO 4T1 Cell Line Syngeneic Transplantation Model Pgp-KO 4T1 cells were cultured with the RPMI1640 medium containing 10% FBS, 1 mM sodium pyruvate, and antibiotics under conditions at 37° C. in a 5% carbon dioxide gas incubator. The cells were collected using trypsin-EDTA when the cells reached to approximately 80% confluency. The medium described above was added to the collected cells to prepare a suspension at 1.0×10$^7$ cells/mL. 0.1 mL of the cell suspension was subcutaneously transplanted at the right body side into 6 mice (BALB/cAJcl, CLEA Japan, Inc.) per each group of the control group, eribulin mesylate liposomal formulation alone administration group, the anti-mouse PD-1 antibody (Bio X cell) alone administration group, and the combined administration of eribulin mesylate liposomal formulation and the anti-mouse PD-1 antibody. From day 4 post-transplantation, eribulin mesylate liposomal formulation (0.3 mg/kg, once a week, twice in total, tail vein injection) and the anti-mouse PD-1 antibody (200 μg/mouse, once a week, twice in total, fail vein injection) were each administered alone or in combination to the alone administration groups or the combined administration group. No drug was administered to the control group. The liposomal composition comprising eribulin mesylate was prepared in accordance with the method as that in Example 1.

On day 3, day 7, day 9, day 13, day 17, day 20, day 24, day 27, day 31, day 34, day 38, day 41, day 44, day 48, and day 51 after administration, with the starting date of administration being day 0, the longest diameter and the short axis of the tumor grown in each mouse were measured with a digimatic caliper (a product made by Mitutoyo Corporation).

The tumor volume was calculated in accordance with the following formula.

Tumor volume (mm$^3$) longest diameter (mm)×short axis$^2$ (mm$^2$)/2

Figure 3:
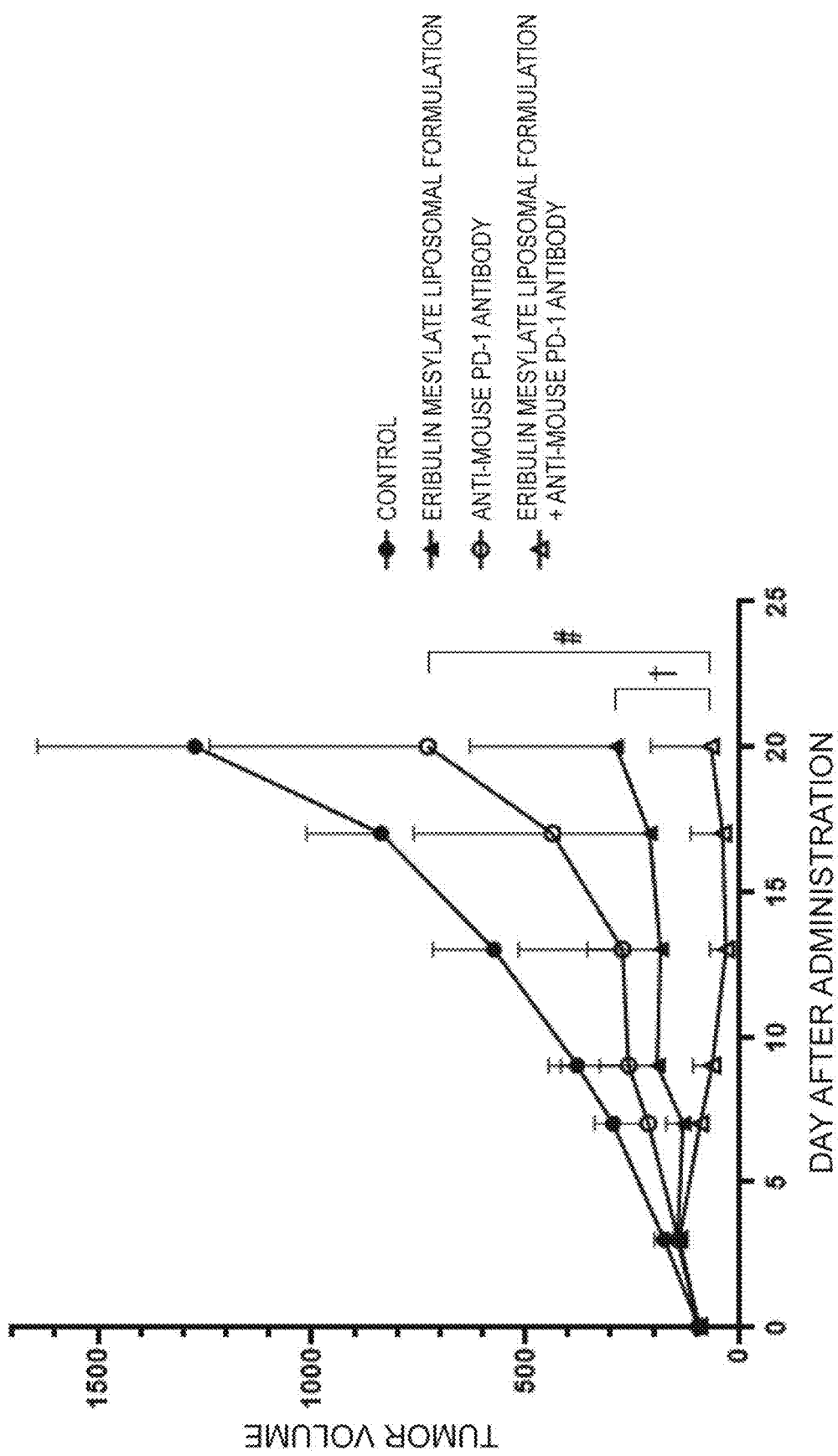
FIG. 3 is a graph illustrating effect of treatment with a combination of a liposomal formulation comprising eribulin mesylate at a dose of 0.3 mg/kg and an anti-PD-1 antibody on tumor growth.

The mean and standard deviation (SD) of the results of measurement of the tumor volume in each group are illustrated in FIG. 3 and the frequencies of mice with tumor disappearance are set forth in Table 3. For statistical analysis, the statistical comparison between the two groups of eribulin mesylate liposomal formulation alone administration group or the anti-mouse PD-1 antibody alone administration group and eribulin mesylate liposomal formulation and anti-mouse PD-1 antibody combined administration group was conducted by repeated measures ANOVA (†, #: p<0.05).

As a result, in the Pgp-KO 4T1 syngeneic tumor transplantation model, the combined administration of a low dose of eribulin mesylate liposomal formulation (0.3 mg/kg) and the anti-mouse PD-1 antibody exhibited excellent antitumor effect in comparison with eribulin mesylate liposomal formulation alone administration group or the anti-mouse PD-1 antibody alone administration group. In FIG. 3, (†) indicates that the combined administration of eribulin mesylate liposomal formulation and the anti-mouse PD-1 antibody statistically significantly inhibited tumor growth in comparison with eribulin mesylate liposomal formulation alone administration and (#) indicates that the combined administration of eribulin mesylate liposomal formulation and the anti-mouse PD-1 antibody statistically significantly inhibited tumor growth in comparison with the anti-mouse PD-1 antibody alone administration. The tumor disappearance was observed in the combined administration group of eribulin mesylate liposomal formulation (0.3 mg/kg) and the anti-mouse PD-1 antibody at a frequency higher than other groups.

TABLE 3

Frequency of appearance of mice with tumor disappearance in each group

| Group | Frequency (%) of mice with tumor disappearance |
|---|---|
| Control | 0/6 (0%) |
| Eribulin mesylate liposomal formulation Alone | 1/6 (17%) |
| Anti-mouse PD-1 antibody Alone | 0/6 (0%) |
| Eribulin mesylate liposomal formulation + Anti-mouse PD-1 antibody Combined administration | 4/6 (67%) |

Figure 4:
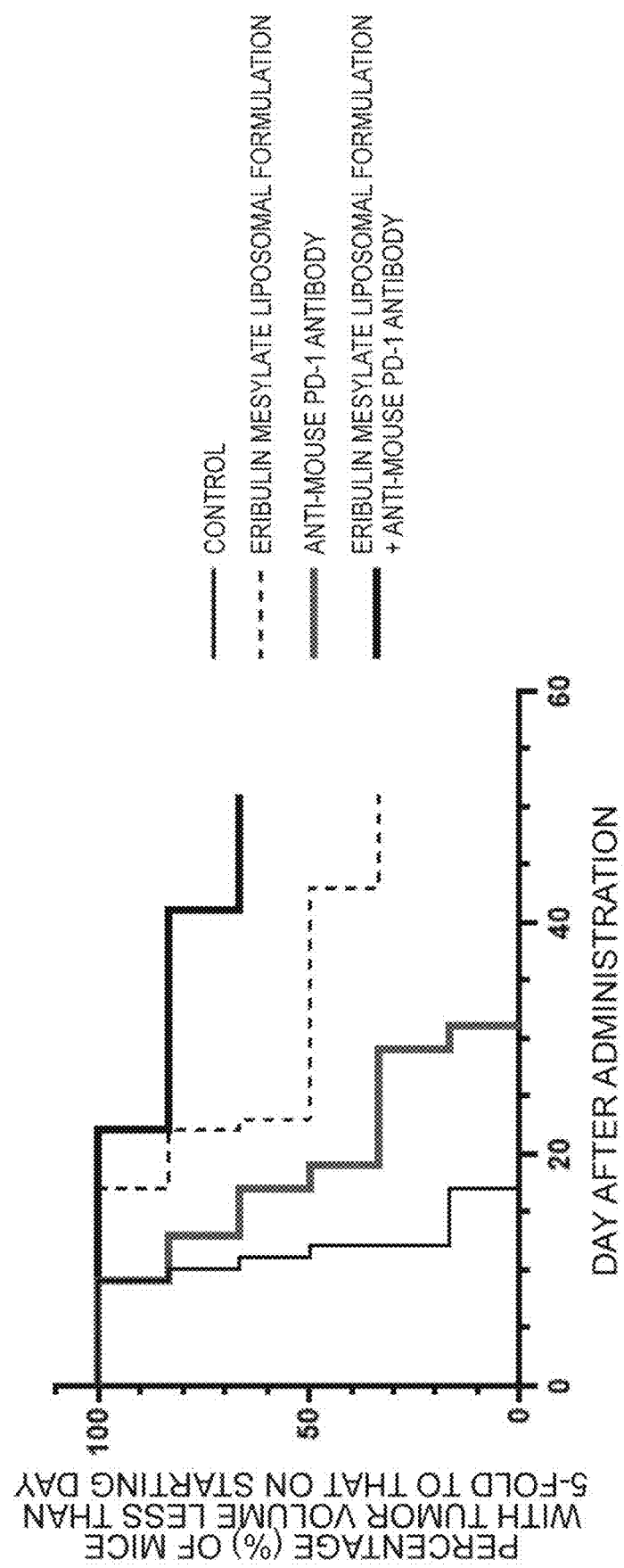
FIG. 4 is a graph illustrating effect of treatment with a combination of a liposomal formulation comprising eribulin mesylate at a dose of 0.3 mg/kg and an anti-PD-1 antibody on T×5.

The result of comparison of the groups for the time until the tumor volume exceeds 5 times that on the starting date of administration (T×5) in the experiment is shown in FIG. 4 and the median of T×5 in each group and the percentage (%) thereof to the control group are set forth in Table 4. For statistical analysis, a log-rank test between the 2 groups of the combined administration group of eribulin mesylate liposomal formulation and the anti-mouse PD-1 antibody to the anti-mouse PD-1 antibody, alone administration group was conducted (#: p<0.05).

As a result, in the Pgp-KO 4T1 syngeneic tumor transplantation model, the combined administration of eribulin mesylate liposomal formulation (0.3 mg/kg) and the anti-mouse PD-1 antibody exhibited the effect of extending suppression time of tumor growth (T×5) in comparison with the control group, eribulin mesylate liposomal formulation alone administration group, the anti-mouse PD-1 antibody alone administration group. # in FIG. 4 indicates that the combined administration of eribulin mesylate liposomal formulation and the anti-mouse PD-1 antibody statistically significantly extended suppression time of tumor growth in comparison with the anti-mouse PD-1 antibody alone administration.

TABLE 4

Effect of combined administration of eribulin mesylate liposomal formulation (0.3 mg/kg) and anti-mouse PD-1 antibody to T × 5

| Group | T × 5 (days) | Ratio to control |
|---|---|---|
| Control | 11.5 | 100% |
| Eribulin mesylate liposomal formulation Alone | 33.0 | 287% |
| Anti-mouse PD-1 antibody Alone | 18.0 | 157% |
| Eribulin mesylate liposomal formulation + Anti-mouse PD-1 antibody Combined administration | >51.0# | >443% |

What is claimed is:

1. A method for treating a tumor, comprising administering a liposomal composition comprising eribulin or a pharmaceutically acceptable salt thereof and a PD-1 antagonist to a patient in need thereof, wherein the PD-1 antagonist is an anti-PD-1 antibody, and wherein the tumor is selected from the group consisting of breast cancer, colorectal cancer, and kidney cancer.

2. The method according to claim 1, wherein the liposomal composition comprising eribulin or a pharmaceutically acceptable salt thereof and the PD-1 antagonist are administered simultaneously.

3. The method according to claim 1, wherein eribulin or the pharmaceutically acceptable salt thereof is eribulin mesylate.

4. The method according to claim 1, wherein the anti-PD-1 antibody is selected from the group consisting of nivolumab, pembrolizumab, cemiplimab, sintilimab, and toripalimab.

5. The method according to claim 1, wherein the tumor is breast cancer.

6. The method according to claim 1, wherein the liposomal composition comprising eribulin or a pharmaceutically acceptable salt thereof and the PD-1 antagonist are administered separately.

7. The method according to claim 4, wherein the tumor is breast cancer.

8. The method according to claim 1, wherein the tumor is colorectal cancer.

9. The method according to claim 4, wherein the tumor is colorectal cancer.

10. The method according to claim 1, wherein the tumor is kidney cancer.

11. The method according to claim 4, wherein the tumor is kidney cancer.

12. The method according to claim 5, wherein eribulin or the pharmaceutically acceptable salt thereof is eribulin mesylate.

13. The method according to claim 7, wherein eribulin or the pharmaceutically acceptable salt thereof is eribulin mesylate.

14. The method according to claim 8, wherein eribulin or the pharmaceutically acceptable salt thereof is eribulin mesylate.

15. The method according to claim 9, wherein eribulin or the pharmaceutically acceptable salt thereof is eribulin mesylate.

16. The method according to claim 10, wherein eribulin or the pharmaceutically acceptable salt thereof is eribulin mesylate.

17. The method according to claim 11, wherein eribulin or the pharmaceutically acceptable salt thereof is eribulin mesylate.

* * * * *